US011621410B2

(12) United States Patent
Ghezzi et al.

(10) Patent No.: US 11,621,410 B2
(45) Date of Patent: Apr. 4, 2023

(54) IMPLANTABLE ELECTRODE AND METHOD FOR MANUFACTURING

(71) Applicant: École Polytechnique Fédérale de Lausanne, Lausanne (CH)

(72) Inventors: Diego Ghezzi, Morges (CH); Marta Airaghi Leccardi, Lausanne (CH)

(73) Assignee: École Polytechnique Fédérale de Lausanne, Lausanne (CH)

( * ) Notice: Subject to any disclaimer, the term of this patent is extended or adjusted under 35 U.S.C. 154(b) by 919 days.

(21) Appl. No.: 16/467,360

(22) PCT Filed: Dec. 6, 2016

(86) PCT No.: PCT/EP2016/079942
§ 371 (c)(1),
(2) Date: Jun. 6, 2019

(87) PCT Pub. No.: WO2018/103828
PCT Pub. Date: Jun. 14, 2018

(65) Prior Publication Data

US 2020/0091495 A1 Mar. 19, 2020

(51) Int. Cl.
*A61B 5/24* (2021.01)
*H01M 4/04* (2006.01)
(Continued)

(52) U.S. Cl.
CPC ............. *H01M 4/0404* (2013.01); *A61B 5/24* (2021.01); *A61B 5/6847* (2013.01);
(Continued)

(58) Field of Classification Search
CPC ................................................ A61B 2562/125
See application file for complete search history.

(56) References Cited

U.S. PATENT DOCUMENTS

2010/0200538 A1 8/2010 Petisce et al.
2011/0054579 A1* 3/2011 Kumar .................... A61B 5/24 216/13

(Continued)

FOREIGN PATENT DOCUMENTS

JP H10126058 A 5/1998
JP 2003347734 A 12/2003

*Primary Examiner* — Austin Murata
(74) *Attorney, Agent, or Firm* — Vorys, Sater, Seymour and Pease LLP

(57) ABSTRACT

The invention relates to a method for manufacturing an electrode, preferably an implantable electrode array comprising the following steps: Applying (101) a layer of electrically conducting material (4) above a substrate material (1) for forming the electrically conductive traces; applying (102) a layer of insulating material (6) directly on top of the layer of electrically conducting material (4) for covering the electrically conductive traces; patterning (103) the layer of insulating material (4) by partly exposing the layer of electrically conducting material (4) to form at least one contact area (8) on the layer of the electrically conducting material (4), wherein a mask for patterning the layer of insulating material (6) defines a region (9) in the at least one contact area (8) at which the insulating material (6) in the at least one contact area (8) remains; and partly applying (104) a top layer (13) of electrically conducting material (4) at the contact area (8) on top of the layer of insulating material (6) for coating the remaining insulating material (9) to lift the contact area (8*a*). The invention further relates to an electrode, preferably an implantable electrode array.

10 Claims, 17 Drawing Sheets

(51) Int. Cl.

| | |
|---|---|
| ***A61B 5/00*** | (2006.01) |
| ***A61N 1/05*** | (2006.01) |
| ***H01M 4/1395*** | (2010.01) |
| ***H01M 4/92*** | (2006.01) |

(52) U.S. Cl.

CPC ........ *A61N 1/0551* (2013.01); *H01M 4/1395* (2013.01); *H01M 4/921* (2013.01); *A61B 2562/046* (2013.01); *A61B 2562/125* (2013.01)

(56) References Cited

U.S. PATENT DOCUMENTS

| | | | | |
|---|---|---|---|---|
| 2011/0093052 | A1 | 4/2011 | Anderson et al. | |
| 2013/0303873 | A1 * | 11/2013 | Voros .................. | H05K 1/0283 604/20 |
| 2013/0345780 | A1 | 12/2013 | Tabada et al. | |
| 2014/0277317 | A1 * | 9/2014 | Tooker ................ | A61N 1/0551 607/116 |

* cited by examiner

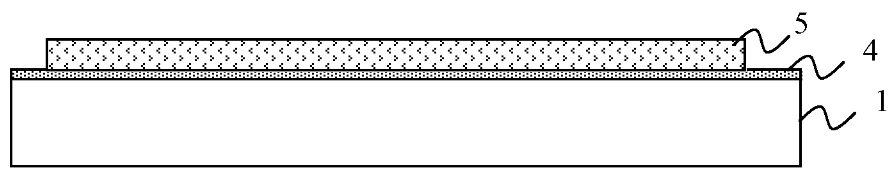
Fig. 2a
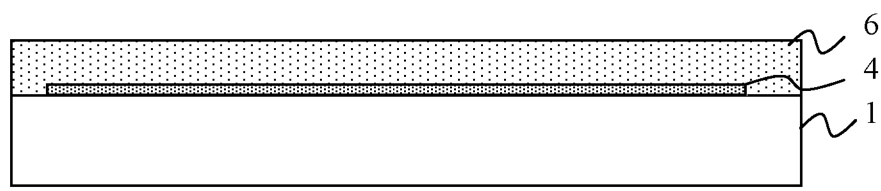
Fig. 2b
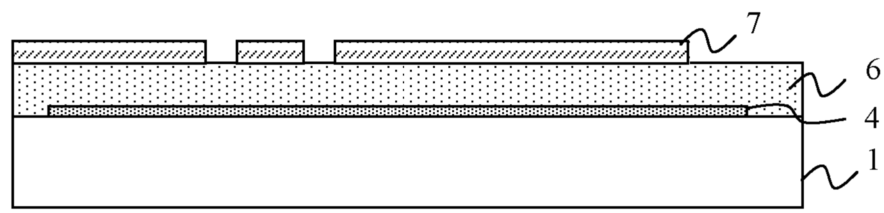
Fig. 2c
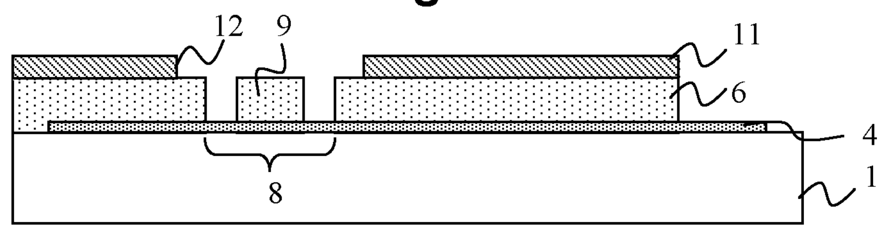
Fig. 2d
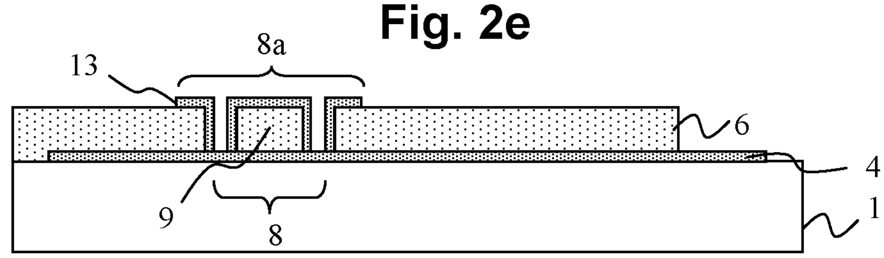
Fig. 2e
Fig. 2f Fig. 12 – Prior Art

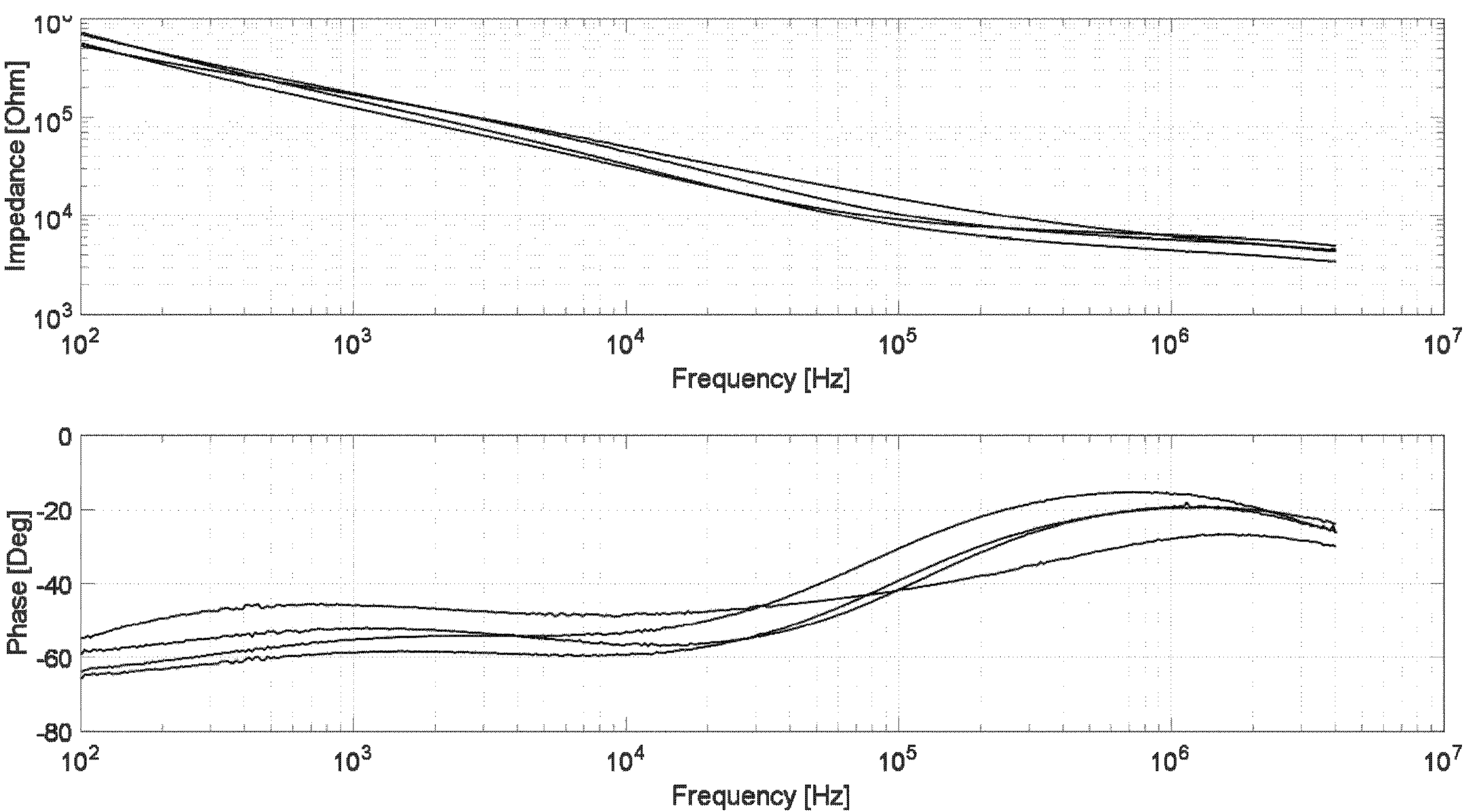
Fig. 14 – Prior Art

IMPLANTABLE ELECTRODE AND METHOD FOR MANUFACTURING

FIELD OF THE INVENTION

The invention is related to a method for manufacturing an electrode, preferably an implantable electrode array, and is further related to an electrode, preferably an electrode array—also known as Multi-Electrode-Array (MEA), more preferably an implantable electrode array. The inventive electrode is sometimes referred to as "implant" or "probe" and can for instance be used for metering and/or recording of an electrical signal derived from an excitable tissue such as a nervous tissue. The implantable electrode can for instance also be used for stimulating of an excitable tissue such as a nervous tissue using an electrical signal. The inventive electrode can be used for both in vitro and in vivo applications and needs to be bio-compatible.

BACKGROUND OF THE INVENTION

A MEA is a device that contains a plurality of contact areas, also referred to as electrodes or contact plates or contact shanks or stimulating elements. Through each contact area an electrical signal is obtained or delivered from/to the tissue. So, a MEA essentially serves as a tissue interface, such as neural interface that connects excitable cells such as neurons to an electronic processing circuitry. In general, there are two main classes of MEAS: implantable electrode (arrays) used in vivo and non-implantable electrode (arrays) used in vitro. Hereinafter, the term "implantable electrode" is referred to both, in vivo and in vitro applications.

In particular, excitable cells such as neurons and muscle cells create an ion current through its cell membranes when excited, causing a change in a voltage between the inside and the outside of each cell. When recording such a neural signal, an electrode on an electrode array transduces this change in voltage from the environment carried by ions (ion current) into a current carried by electrons (electronic current) to obtain an electrical signal from the contact area of the electrode array. When stimulating, a contact area of the electrode array transduces an electronic current into an ionic current, which triggers the voltage-gated ion channel(s) on the membrane(s) of the stimulated (excitable) cell(s), causing the cell to depolarize and trigger an action potential if it is a neuron or a muscle cell.

The size and the shape of the recorded electrical signal, as well as the efficiency of the stimulating signal are dependent on several factors. One of these factors is the nature of the medium in which the cell is located, e.g. the medium's electrical conductivity, capacitance and homogeneity. Another influencing factor is the nature of the contact between the cell(s) and the contact area of the electrode array, e.g. the area size of the contact and the distance to the cell(s). Another influencing factor is the nature of the electrode itself, e.g. its geometry, impedance and noise. Another influencing factor is the subsequent (or generating) signal processing unit, e.g. its gain, bandwidth, cut-frequency, data sampling property.

A main factor that limits the increase in the amount of contact areas in an electrode array is the limited space for interconnections due to the small size of the MEA. On the one hand, these interconnections limit the area available for the electrodes on the array itself. On the other hand, if contacting the contact area with a subsequent processing unit for further signal processing or signal generation, the physiological necessity of keeping a reduced cut through the tissue needs to be met.

In Kisban et al. "*Microprobe Array with Low Impedance Electrodes and Highly Flexible Polyimide Cables for Acute Neural Recording*", published in 29th Annual International Conference of the IEEE Engineering in Medicine and Biology Society, 2007, pp. 175 to 178 or in Shah et al. "*Improved chronic neural stimulation using high surface area platinum electrodes*", published in 35th Annual International Conference of the IEEE Engineering in Medicine and Biology Society, 2013, pp. 1546 to 1549 a silicon-based (Kisban et al.) or a polyimide-based (Shah et al.) microprobe with linear distribution of contact areas at the electrode array is introduced. The implantable electrode array is made of platinum (Pt) or platinum black (Pt black). Platinum black (Pt black) is a fine powder of platinum with good catalytic properties used as coating material of platinum electrodes. The electrode array further comprises polyimide (PI)—a polymer of imide monomers. The electrode array is planar. Thus, the number of contact areas in the electrode array is very limited.

A. Bendali et al., "*Synthetic 3D diamond-based electrodes for flexible retinal neuro-prostheses: Model, production and in vivo biocompatibility*", published in Biomaterials, vol. 67, pp. 73 to 83 of October 2015 discloses modelling of a planar or 3D implants with distant ground to demonstrate greater spatial resolution with 3D structures. The 3D shape is given by a negative molding of the implant substrate. A multi-layer molding with such a type of process is impossible. Thus, the number of contact areas in the electrode array is very limited, too.

A valid solution to increase the density of the electrode array is to produce the electrode array with conductive traces placed on different layers. In a bi-layer system for example, the implant could consist of double the amount of contact areas for the same width of connection cables. Going multi-layer allows the underlying interconnections to be designed passing below the other ones and even below the contact areas. The higher density allows a much better spatial resolution and allows the use of a much higher number of channels for a more efficient and targeted stimulation or a more reliable and precise recording.

Z. Xiang et al., "*A flexible three-dimensional electrode mesh: An enabling technology for wireless brain-computer interface prostheses*", published in Microsystems & Nanoengineering, vol. 2, page 16012 in May 2016 and Z. Xiang et al., "*Progress of Flexible Electronics in Neural Interfacing—A Self-Adaptive Non-Invasive Neural Ribbon Electrode for Small Nerves Recording", published in Adv. Mater., vol.* 28, no. 22, pp. 4472 to 4479 in June 2016 describe electrodes that are made by an epoxy-based negative photoresist (SU8), which is deposited and coated after the completed microfabrication of standard probes. Using such a photoresist to fabricate a 3D electrode array implies that in a multi-layer system it is required to deposit and pattern the contact areas separately for each specific layer. The thickness and exposure doses vary depending on the layer depth. Moreover, the deposition over different depths might not be homogeneous and the SU8 risk to detach at any time later. So, the manufacturing of such MEAS is imprecise, cost intense and requires very high material efforts.

Also A. Tooker et al., "*Optimization of multi-layer metal neural probe design*", published Annual International Conference of the IEEE Engineering in Medicine and Biology Society pp. 5995 to 5998 in 2012 describes a microfabrication process for a multi-layer metal, multi-site, polymer-based MEA.

Due to the necessary insulating encapsulation of conductive layers, which covers the conductive traces, but needs to be open for providing/obtaining the electrical signal to/from the tissue, the known multi-layer MEA has significant drawbacks. For the intermediate conductive layers placed closer to the bottom of the electrode array, the aspect ratio between the diameter of the contact area at the conductive layer and the encapsulating thickness of the above insulating material becomes more and more problematic. Further, the efficiency of a stimulating/recording of the tissue is highly dependent on the distance between the contact area and the tissue cell. This distance is highly affected by the encapsulation-openings aspect ratio.

In US 2016/0120423 A1, a layered structure comprises electrical conductivity material layers and insulating material layers. Access areas are built for each electrically conductivity material layer during/after the appliance of additional layers. This increases the complexity of the manufacturing process. A main surface of the MEA is built with contact areas, wherein each electrical conductivity material layer is contacted by vias. Each contact area and the respective via is built using an electroplating or inkjet printing process.

All known techniques for providing a multi-layered structure comprise interconnections through the different layers that are made by vias. Each via is etched with every additional layer. These vias are often electroplated. This involves a high amount of material to deposit and a high number of manufacturing steps. Furthermore, a high mechanical mismatch with the bendable PI is to be expected as well as more thermal expansions, which reduce the quality of the MEA enormous.

It is thus a need to manufacture an (implantable) electrode (array) for recording/metering and/or stimulating of a nervous tissue having a higher density (and thus a higher spatial resolution) of contact areas in a more efficient manner. In particular manufacturing steps and material efforts should be reduced drastically but it should be also ensured that the distance between the contact area and the tissue cell is drastically reduced.

So it is an object of the present application to provide an electrode, preferably an electrode array, and a respective method for manufacturing that overcomes the above mentioned problems, especially by drastically reducing the number of manufacturing steps and also reducing the distance between contact area and nervous tissue for stimulating and recording purposes.

SUMMARY OF THE INVENTION

The above-identified problems are solved by the features of the independent claims. Further advantageous embodiments are derived from the respective dependent claims.

In an aspect of the present invention, a method for manufacturing an electrode, preferably an implantable electrode array comprises the following steps: In a first method step, a layer of electrically conducting material is applied above a substrate material for forming an electrically conductive trace. In a second method step, a layer of insulating material is directly applied on top of the layer of electrically conducting material for covering the electrically conductive trace. In a third method step, the layer of insulating material is patterned by partly exposing the layer of electrically conducting material forming at least one contact area on the layer of electrically conducting material, wherein a mask for patterning the layer of insulating material defines a region in the at least one contact area at which the insulating material in the at least one contact area remains. In a fourth method step, a top layer of electrically conducting material is partly applied at the at least one contact area directly on top of the layer of insulating material for coating the remaining insulating material in the region to lift the contact area.

The electrode is preferably a part of a multi-electrode array, MEA. This electrode array is used for recording, metering, and/or stimulating of a nervous tissue with an electrical signal that is transmitted via the conductive trace in the electrically conducting layer. This electrical signal is generated from a processing unit, in case of stimulating the nervous/muscle tissue. This electrical signal is provided to a processing unit, in case of recording/metering the nervous/muscle tissue. The electrode is thus a mean for transducing an ion current into/from an electric current.

The application of the electrically conducting material may be achieved by a sputtering process, preferably a physical vapor deposition (PVD) process, more preferably a magnetron sputter deposition process, e.g. High Power Impulse Magnetron Sputtering (HIP-IMS). An important advantage of sputtering is that materials with very high melting points are easily sputtered while evaporation of these materials in a resistance evaporator may raise problems. Sputter deposited layers have a composition close to that of the source material. Sputtered layers may have excellent adhesion properties with the layer below. A target contains a large amount of material and is maintenance free, making the technique suited for ultrahigh vacuum applications. Sputtering sources contain no high-temperature parts and are compatible with polymeric substrates and reactive gases such as oxygen. Sputtering can be performed top-down while evaporation is performed bottom-up. Advanced processes such as epitaxial growth are possible.

The electrically conducting material is preferably Pt, titanium (Ti), gold (Au) or Pt-Iridium (Ir) or an alloy thereof. More preferably, the electrically conducting material is coated by Ti, Ti-Nitride, Iridium-oxide and Pt black material to obtain proper efficiency, biocompatibility, such as low degradation, low corrosion but high mechanical robustness, and/or a better adhesion with polymeric materials used as substrate and encapsulation. The electrically conducting material provides a robustness and stiffness to the electrode as well as the required elasticity when implanting. Additionally, the material provides excellent properties for transmitting the electrical signal without a high degree of signal degradation.

The substrate material may be used as a carrier material during the manufacturing process. The appliance of the layer of electrically conductive material above the substrate material may imply an appliance of additional layers between the layer of electrically conducting material and the substrate material.

The step of applying the insulating material layer may be achieved by a spin-coating or a printing process to deposit a thin layer of insulating material in a uniform manner to the flat surface below. Usually, a small amount of the material is applied on the center, the substrate is then rotated at high speed in order to spread the insulating material by centrifugal force. The insulating material is preferably polyimide (PI). Alternatively, Polydimethylsiloxane (PDMS) is used as insulating material which is a silicon-based organic polymer that are commonly referred to as silicones. Alternatively, Parylene is used as insulating material, being a variety of chemical vapor deposited poly(p-xylylene) polymers. Alternatively, a liquid crystal polymer (LCP) is used as insulating material being a member of the aromatic polymers. PI, Parylene, LCP and PDMS are highly flexible and thus a preferred material for implantable electrode arrays.

The step of patterning the insulating material layer may be derived by applying a silicon (Si) hard mask sputtering process. The patterning of the insulating layer may thus be achieved by Si dry etching process followed by PI dry etching process which provides a high degree on preciseness. The underlying electrically conducting layer acts as an etch-stop layer which reduces the manufacturing steps drastically.

The term patterning hereinafter is referred to a process of structuring of an existing layer using photolithographic processes. Photolithography is basically a photographic process by which a light sensitive polymer, called a photoresist, is exposed and developed to form 3D relief images on a flat layer. In general, the ideal photoresist image has the exact shape of the designed or intended pattern in the plane of the substrate, with vertical walls through the thickness of the resist. Thus, the final resist pattern is binary: parts of the substrate are covered with resist while other parts are completely uncovered. This binary pattern is needed for pattern transfer since the parts of the substrate covered with resist will be protected from etching, ion implantation, or other pattern transfer mechanism. The general sequence of processing steps for a typical photolithography process is as follows: substrate preparation, photoresist spin-coat, prebake (softbake), exposure, post-exposure bake, development, and postbake (hardbake). A resist strip (removal) is the final operation in the lithographic process, after the resist pattern has been transferred into the underlying layer. This sequence is generally performed on several tools linked together into a contiguous unit.

The partly exposing of the layer of electrical conducting material inter alia requires an uncovering of this layer at least at one contact area by partly removing the layer of the insulating material. The mask for patterning the insulating material layer is defined in such a manner that insulating material remains (is not removed) in predefined region of the contact area, preferably in the center of the contact area. Preferably, after partly removal of the insulating layer, a pillar of insulating material remains at the predefined region inside each contact area.

Each electrically conductive layer comprises at least one contact area. Preferably, a plurality of contact areas in each electrically conductive layer is provided to increase the density and thus the spatial resolution of the electrode array.

By partly applying a top layer of electrically conducting material on top and around the pillar of insulating material, the layer of electrically material is lifted from a contact area of the layer itself to a main surface of the electrode array or even above this main surface. The remaining insulating material is thus covered by the top layer. A main surface of the electrode array is an outer surface of the electrode array that faces towards a nervous tissue.

The inventive method heavily reduces the material efforts of the electrically conductive material since the contact area on this layer has a predefined region of remaining insulating material. The remaining insulating material-which is of cheaper material than the electrically conductive material-reduces the material efforts of conductive material which reduces manufacturing costs and increases the flexibility of the electrode array.

By lifting the contact area, the resulting distance between the nervous tissue and the electrode (array) is reduced to a minimal extend and so the efficiency of signal transmission of the electrode is highly increased. So, a multi-layer electrode array is provided that is fabricated in a 3D-shape to allow all the contact areas to be lifted to its main surface or to even protrude the contact area from the main surface (insulating layer) of the electrode array.

In a preferred embodiment, the step of patterning the layer of insulating material further includes a covering of remaining insulating material in the at least one contact area, preferably using a photoresist material, and reducing the thickness of the uncovered regions of the layer of insulating material. This leads to a defined protrusion of the lifted contact area above the main surface of the electrode, especially above the insulating material of the implantable electrode. So, the lifted contact area is arranged above the insulating material, wherein the protrusion is adjustable by the respective thickness reduction. Thus, the protruding contact area can now be embedded in the nervous/muscle tissue, which increases the signal transmission efficiency and location stability of the electrode in the tissue. This may be essential for an in vivo application.

In a preferred embodiment, the step of partly applying the top layer of electrically conducting material is obtained through a respective opening in a stencil mask. This stencil mask is used to precisely define the final contact pad on top of the electrode and the accurate appliance of the top layer of electrically conducting material.

In a preferred embodiment, before the insulating material is patterned, a second layer of electrically conducting material is directly applied on top of the insulating material and second layer of insulating material is directly applied on top of the second layer of electrically conducting material. So, a second layer of conductive traces can be formed in a second layer different from the first layer of electrically conductive material. Thus, the multi-layered structure of the resulting electrode is extended by an additional conductive layer. This results in a higher number of contact areas per total area of the electrode array and/or allows a higher density which result in an improved spatial resolution of the electrode array.

In a preferred embodiment, the step of applying of the second layer of electrically conducting material and the step of applying of the second layer of insulating material is at least once, preferably twice, repeated before the step of patterning the insulating material is processed. Thus, at least three layers, preferably four layers, of conductive traces can be formed in the electrode array. The electrically conducting material may act as an etch stop layer during patterning the insulating layer. Since the insulating layers are all patterned at once, the number of manufacturing steps is advantageously reduced.

The patterning step of the insulating material is applied at once after all layers of insulating materials and all layers of electrically conducting materials are applied to the multi-layered structure. By defining regions of remaining insulating material (to produce pillars) for each contact area, preferably in the center of the contact areas, the patterning for removing the insulating material in contact regions, which is achieved by etching rings instead of complete holes to access the contact area, allows the realization of a multi-layered MEA in a simple and efficient manner. Since Pt is inert to oxygen plasma etching at least for certain limits, the Pt can be used as an etch-stop layer which reduces the number of manufacturing processes in its entirety, especially in the resulting number of photolithography processes. However, a strong oxygen plasma etching applied for longer times may also reduce the Pt thickness. This is dependent on the tool, power, gas flow and temperature that are applied.

In a preferred embodiment, the step of patterning of the insulating material includes patterning of all layers of insulating material at once by partly exposing the respective layer of electrically conducting material to obtain a contact area on each layer of electrically conducting material, wherein the mask for patterning all the layers of insulating material defines a region (e.g. a resulting pillar for each contact area through all other insulating layers) in the at least one contact area of each layer of electrically conducting material at which the insulating material in the respective contact area remains and is thus not removed.

So, all contact areas of a resulting multi-layer electrode array can be lifted to the same level which reduces signal transmission differences between the individual contact areas.

In a preferred embodiment, before processing the step of applying the layer of electrically conducting material, a bottom layer of insulating material is applied directly on top of the substrate material. So, the conductive trace is covered in case of removal of the substrate in a manufacturing step.

In a preferred embodiment, the step of applying of the layer of electrically conducting material further includes a patterning step. Thus, length/width of a conductive trace is defined and an overlapping of a trace with a contact area of the MEA is avoided.

In a preferred embodiment, the substrate material is removed to obtain the implantable electrode. This may be achieved by an aluminum-anodic dissolution process.

In another aspect of the invention, an electrode, preferably an electrode array, comprises at least one electrically conductive layer comprising at least one electrically conductive trace to transmit an electrical signal, wherein the at least one electrically conductive layer is encapsulated by an insulating material. The implantable electrode array further comprises at least one contact area for interfacing the electrical signal with a nervous tissue, wherein the at least one contact area comprises a region, e.g. a pillar of coated insulating material to lift the at least one contact area to a main surface of the implantable electrode.

The electrode further comprises at least one connecting area for interfacing the electrical signal with an external processing unit.

In a preferred embodiment, the at least one conductive layer is encapsulated between two layers of the insulating material to secure the signal transmission through the tissue or outer influences.

In a preferred embodiment, the at least one lifted contact area protrudes from the main surface of the electrode. This increases the efficiency of the signal interfacing between the nervous tissue and the contacting area.

Preferably, an electrode array further comprises at least two electrically conducting traces in two different layers, wherein the different layers are each separated by a layer of insulating material.

Preferably, the at least one conductive trace is made from Pt, Ti, Pt/Ir, or Au. The traces may be coated by Ti, Ti-Nitride, Ir-oxide or Pt black.

Preferably, the insulating material is made from PI, Parylene, LCP and/or PDMS.

The proposed manufacturing can produce multi-layer electrode arrays within one single dry etching step that also defines the outer shape of the electrode array without a need for additional cutting. With an extra step of photolithography and dry etching the electrodes can protrude from the encapsulation layer to an equal arbitrary height (protrusion distance).

Another advantage of the electrode array made in the insulating PI material is a higher surface area available on the electrodes sites due to the walls porosity of the PI pillars after a dry etching process. This implies that the electrode array can have a better injection capacity with respect to flat electrodes.

Furthermore, with the inventive solution, no electroplating is needed to fill the entire volume of the openings, in order to reach the top surface of the MEA. There are fewer problems due to any local mechanical mismatch of the layers of electrically conductive material and the layer of insulating material. Avoiding electroplating reduces manufacturing costs, since the technique is more expensive as it involves more material to deposit.

BRIEF DESCRIPTION OF THE DRAWINGS

In the following, exemplary embodiments of the invention are described with reference to the drawings. The exemplary embodiments do not limit the scope of the invention.

The same reference signs in different drawings indicate the same elements for at least the same functions unless otherwise stated. Individual elements in the drawings may be shown with an increased size to better illustrate the function of the element.

FIG. 2*a*-2*f* show a first exemplary embodiment of a manufacturing process for manufacturing an electrode according to the invention.

FIG. 14 shows an exemplary impedance spectrometry characteristics of a single-layered planar electrode array according to the prior art.

DETAILED DESCRIPTION OF THE PREFERRED EMBODIMENTS

Figure 1:
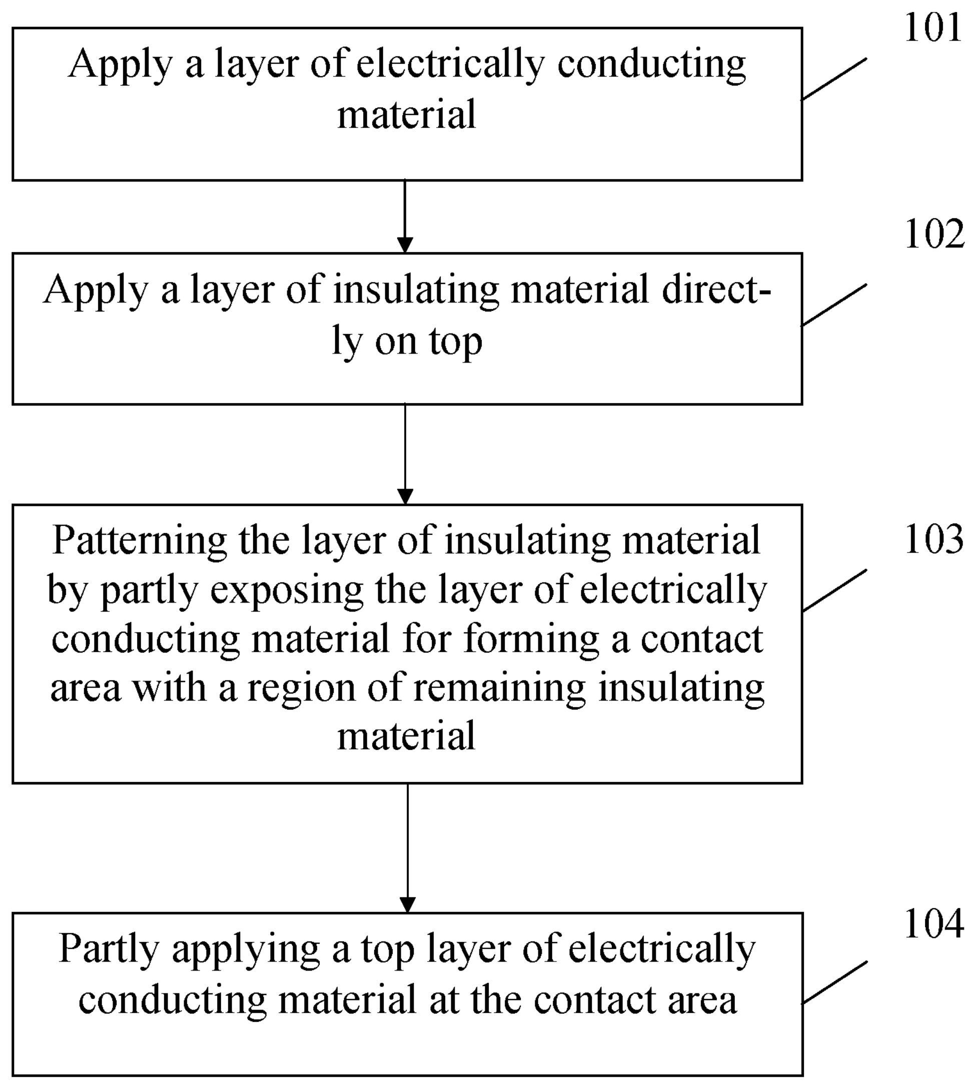
FIG. 1 shows an exemplary embodiment of a process flow of a method for manufacturing an electrode according to the invention.

FIG. 1 shows an exemplary embodiment of a process flow of a method for manufacturing an electrode according to the invention. In step 101, a layer 4 of electrically conducting material is applied above a substrate material 1 for forming an electrically conductive trace 16. In step 102, a layer 6 of insulating material is directly applied on top of the layer 4 of electrically conducting material for covering the electrically conductive trace 16 (not shown).

In step 103, the layer 6 of insulating material is patterned by partly exposing the layer 4 of electrically conducting material to form at least one contact area 8 that has a region 9 with remaining insulating material. In step 104, a top layer 13 of electrically conducting material is partly applied at the contact area 8.

Inventively the insulating material is kept (is remaining) in a region 9, such as a pillar of insulating material, in the middle of a contact area 8 for making the electrode. Therefore, a mask for patterning the layer 6 of insulating material is adapted in order to expose the layer 4 of electrically conducting material in a manner that only rings are removed instead of complete holes. So, remaining insulating material can be left in the contact area. By applying a top layer according to step 104, the remaining insulating is covered by electrically conductive material to lift the contact area to a main surface of the electrode. So, conductive material can be saved which reduces material efforts drastically. Additionally, manufacturing steps can be avoided. This allows the realization of an electrode in a very simple and efficient manner. The distance of the lifted contact area to the tissue is thus highly reduced and signal degradation is prevented.

Furthermore, the lower distance between the lifted contact area and the tissue requires a lower voltage for stimulating or recording. Thus, the degradation of the electrode material is reduced and the risk to induce hydrolysis is lowered.

FIG. 2*a* to FIG. 2*f* show a first exemplary embodiment of a manufacturing process for manufacturing an electrode according to the invention. According to FIG. 2*a*, a substrate 1 is provided. The substrate 1 is preferably a silicone (Si) wafer and may be covered by a further layer as will be described with reference to FIG. 4. Above the substrate 1, a layer 4 of electrically conducting material is applied. The appliance of this layer 4 is described in greater details with reference to FIG. 4. The material of the electrically conducting layer may be a platinum (Pt) or a titanium (Ti). Alternatively, gold (Au) or Pt/Ir alloy may be used as a material of the electrically conducting layer 4.

According to FIG. 2*b*, the electrically conducting layer 4 is covered by a photoresist layer 5. This photoresist layer 5 may be applied during a photolithography process to structure (pattern) the electrically conducting layer 4 and for forming at least one electrically conductive trace 16 (not shown).

In FIG. 2*c*, the photoresist layer 5 has been removed and an etching process has been applied to pattern the electrically conducting layer 4. Further, an insulating layer 6 is applied directly on top of the patterned electrically conducting layer 4. The insulating layer 6 is preferably of polyimide (PI) material or PDMS.

In FIG. 2*d*, a silicone (Si) layer 7 is applied directly on top of the insulating layer 6. The Si layer 7 is patterned in another photolithography process. The patterned Si layer 7 is used as a mask for defining regions of the insulating layer 6 that should be removed and for defining regions of the insulating material layer 6 that should not be removed (and thus remain).

In FIG. 2*e*, the insulating layer 6 has been patterned by partly exposing the layer 4 of electrically conducting material for forming at least one contact area 8 on the layer 4 to access this layer 4. Inventively, the contact area 8 is not exposed in its entirety. So, instead of etching complete holes to form the contact area 8 for accessing the layer 4 of electrically conducting material, regions 9 remain in the center of the contact area 8. Consequently, during this patterning step only rings instead of holes of the insulating material 6 are removed. The region 9 is for instance a pillar of insulating material 6 in the center of the contact area 8. Additionally, in FIG. 2*e* a stencil mask 11 is applied on top of the insulating material 6. The stencil mask 11 has an opening 12 that is arranged (aligned) above the contact area 8. The manufacturing of a stencil mask 11 is explained in greater details in FIG. 9 of this present application.

In FIG. 2*f*, a top layer 13 is partly applied on top of the insulating material 6 and coats (covers) the remaining insulating material in the region 9 of the contact area 8. The top layer 13 is electrically connected to the layer 4 of the electrically conductive material. As a result, the contact area 8 is lifted and a lifted contact area 8*a* is obtained. According to FIG. 2*f*, the contact area 8*a* is lifted to a level equal to a level of a main surface 14 of the electrode. In principle, the material used in this step can be the same material as in layer 4. Alternatively, another material for interface matching may be used, e.g. Ti-Nitride, Iridium-oxide, Pt black, Pt grey.

According to FIG. 2*a* to 2*f*, an inventive manufacturing process for manufacturing a mono-layer implantable electrode is shown. In a final step (not shown) the substrate 1 is removed or replaced by another insulating material layer 3 to obtain a mono-layered electrode according to the invention.

FIG. 3*a* to FIG. 3*g* show a second exemplary embodiment of a manufacturing process for manufacturing an electrode according to the invention. It should be noted that the manufacturing steps according to FIG. 3*a* to FIG. 3*d* are identical to the manufacturing processes as shown in FIG. 2*a* to FIG. 2*d*. To avoid unnecessary repetition of these manufacturing processes, for further explanations of the FIG. 3*a* to FIG. 3*d*, it is referred to FIG. 2*a* to FIG. 2*d* respectively.

In contrast to the manufacturing process as shown in FIG. 2*e*, the manufacturing process in FIG. 3 includes the additional step of covering of the remaining insulating material region 9 with another photoresist layer 5. The insulating layer 6 according to FIG. 3*e* has a thickness of d1.

Figure 3A:
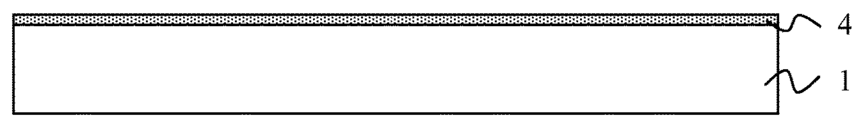
FIG. 3*a*-3*g* show a second exemplary embodiment of a manufacturing process for manufacturing an electrode according to the invention.
Figure 3B:
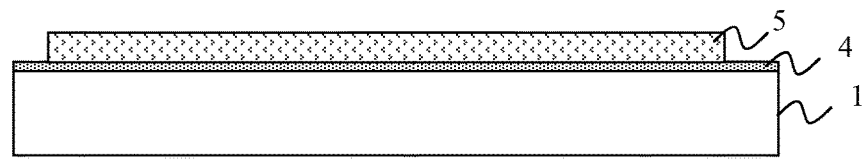
Figure 3C:
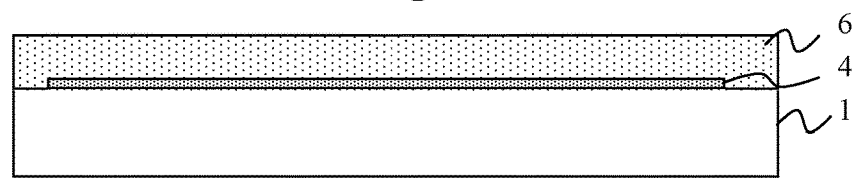
Figure 3D:
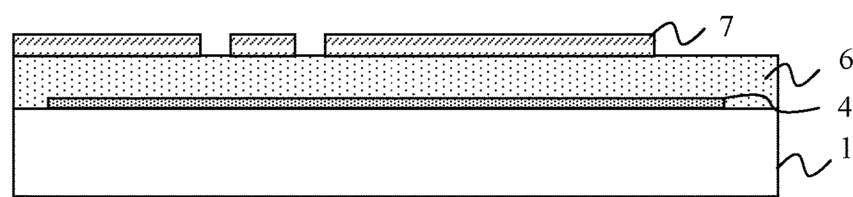
Figure 3E:
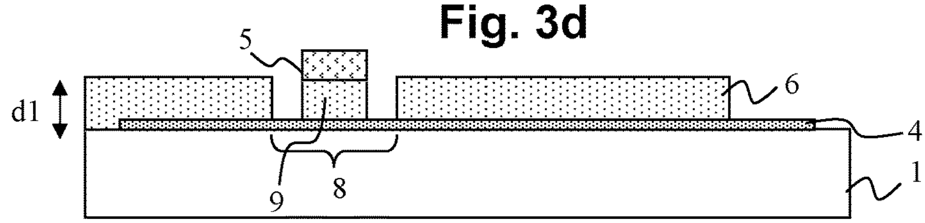
Figure 3F:
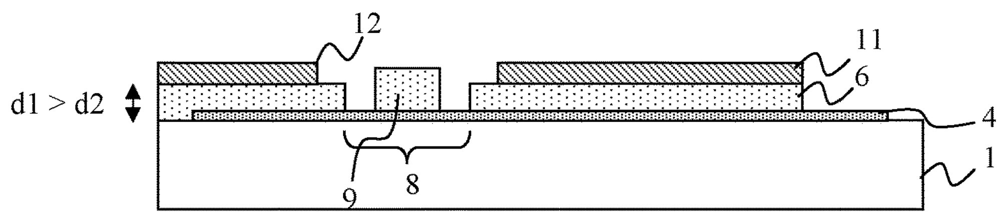

According to FIG. 3*f*, the thickness d1 of the insulating layer 6 is reduced to a thickness d2 smaller than thickness d1. This reduction in thickness may be achieved by a patterning step, wherein the photoresist layer 5 on top of the region 9 protects the underlying insulating material 6 from being reduced in thickness. As a result, the thickness of the layer 6 is d2 for the uncovered regions and is d1 for the covered region 9. The reduction in thickness is adjusted by an etching process applied to remove the insulating material layer 6.

The manufacturing step according to FIG. 3*f* is identical to the manufacturing step in FIG. 2*e*, wherein a stencil mask 11 is applied having an opening 12 arranged on top of the contact area 8.

Figure 3G:
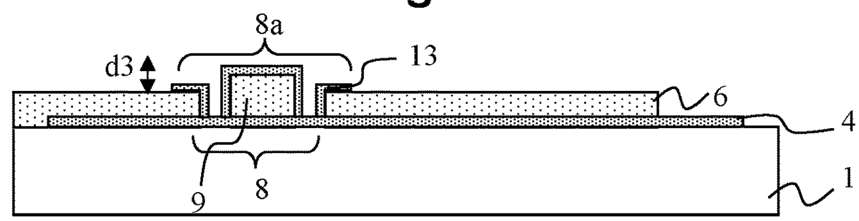

In FIG. 3*g*, a top layer 13 of electrically conducting material is applied for coating the remaining insulating material in region 9 to lift the contact area 8 to a lifted contact area 8*a* as already described in FIG. 2*f*.

As can be derived in FIG. 3*g*, the uncovered regions of the insulating material 6 are reduced to a thickness of d2, wherein the regions 9 are protruding from the main surface 14 with a protrusion distance d3. This protrusion distance d3 leads to a higher location stability of the electrode in the nervous tissue and further improves the signal transmission between the tissue (not shown) and a processing unit (not shown).

Figure 13:
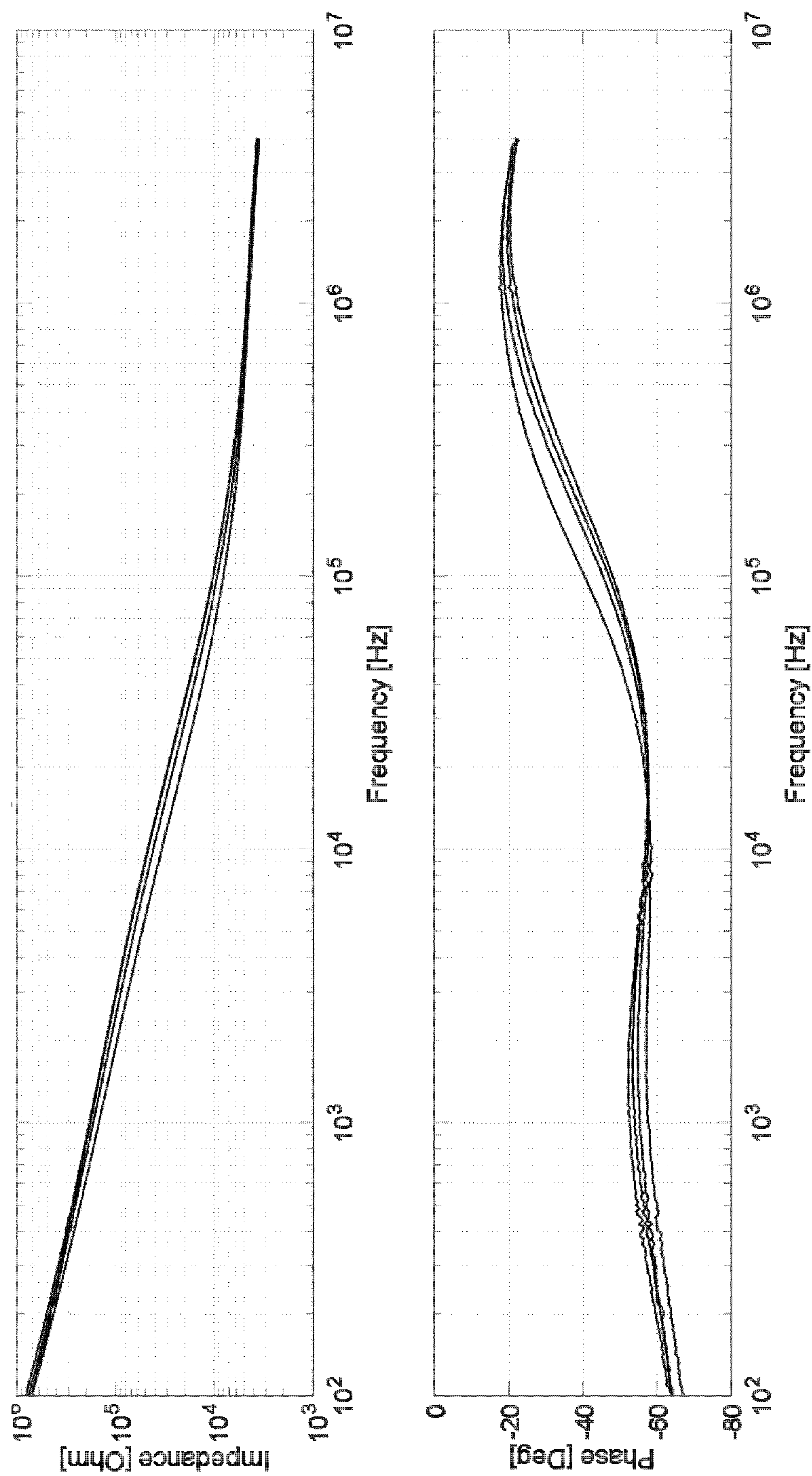
FIG. 13 shows an exemplary impedance spectrometry characteristics of a single-layered 3D electrode array according to the invention.

The electrical characteristics of the mono-layered 3D electrode as manufactured according to FIG. 2 (or FIG. 3) are shown in FIG. 13. The electrical characteristics of a conventional mono-layered planar electrode is shown in FIG. 14 to compare the improvement over the conventional electrode.

Figure 4A:
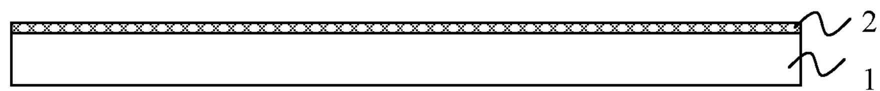
FIG. 4*a*-4*z* show a first exemplary embodiment of a manufacturing process for manufacturing a multi-layered electrode array according to the invention.
Figure 4B:
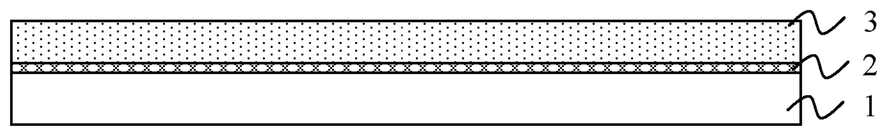
Figure 4C:
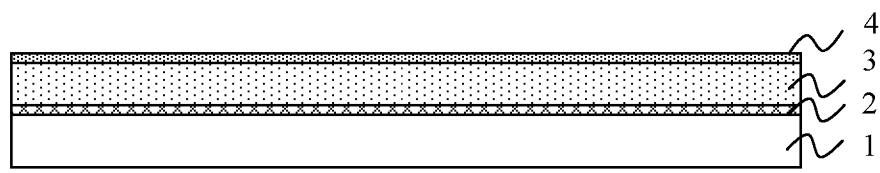
Figure 4D:
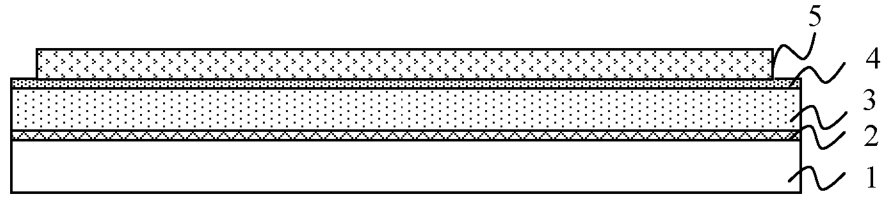
Figure 4E:
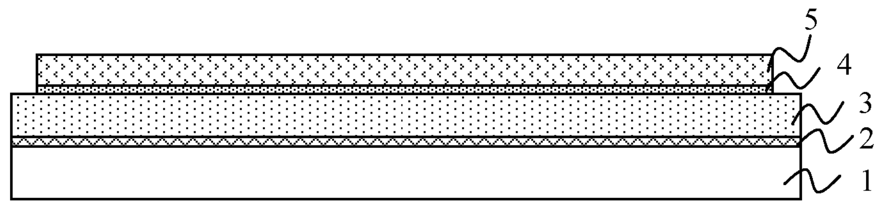
Figure 4F:
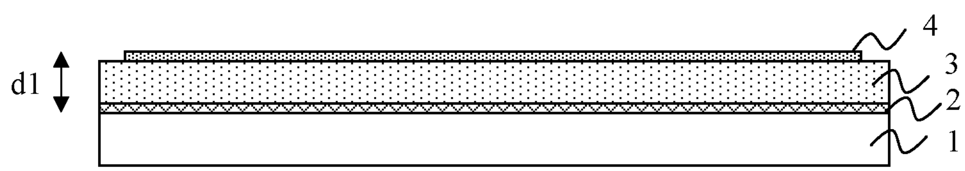
Figure 4G:
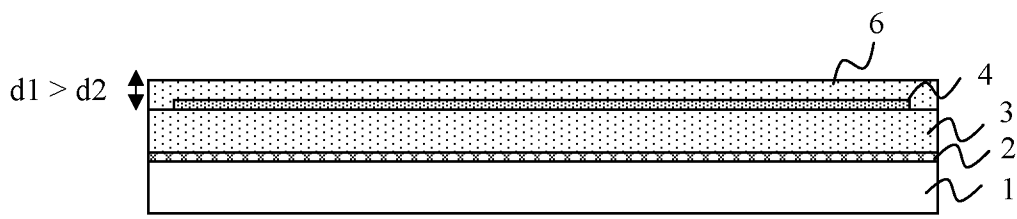
Figure 4H:
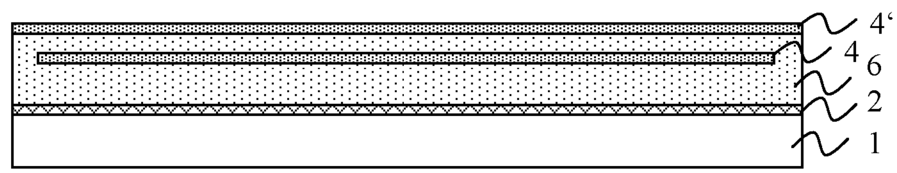
Figure 4I:
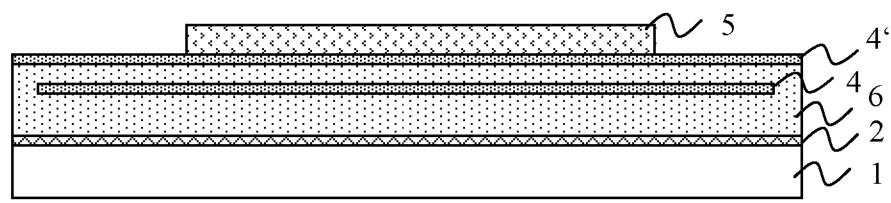
Figure 4J:
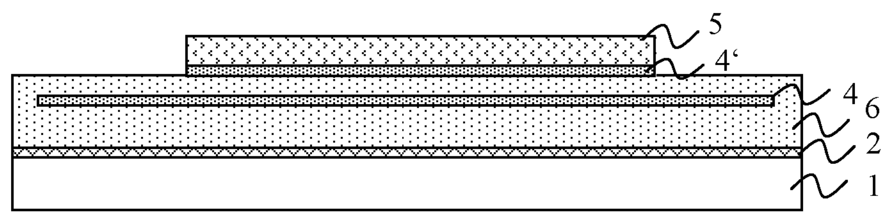
Figure 4K:
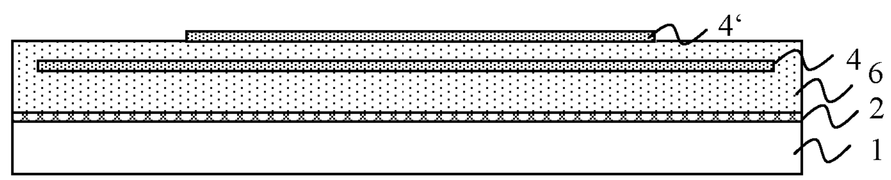
Figure 4L:
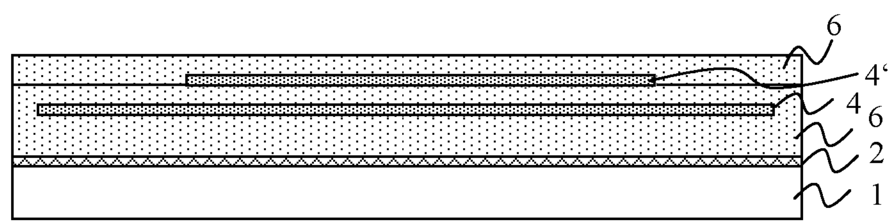
Figure 4M:
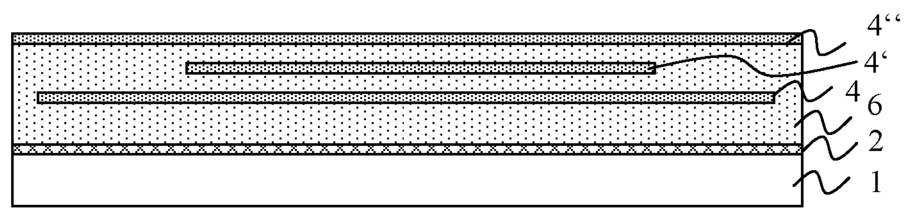
Figure 4N:
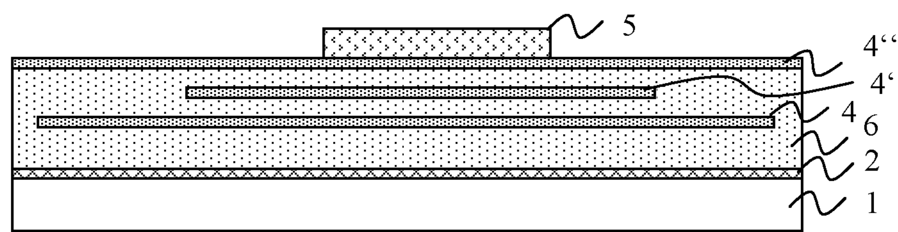
Figure 4O:
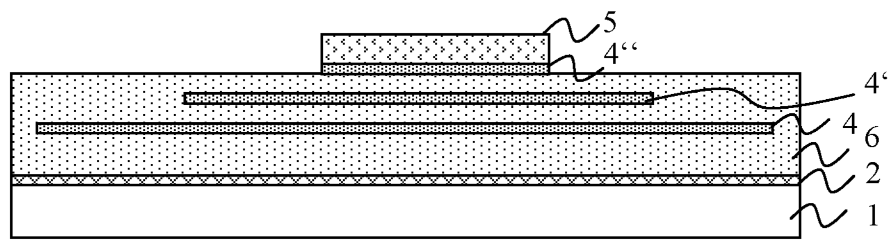
Figure 4P:
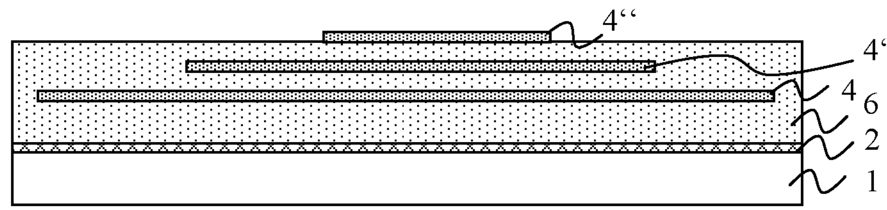
Figure 4Q:
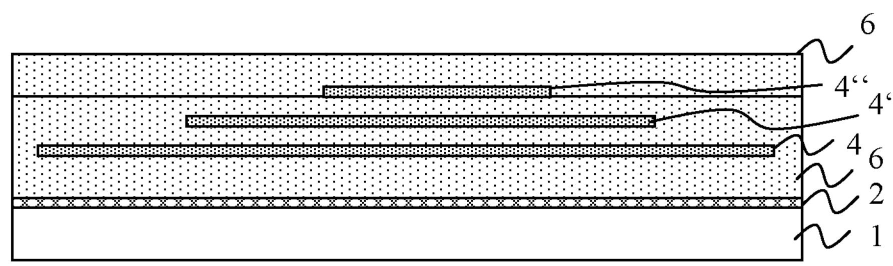
Figure 4R:
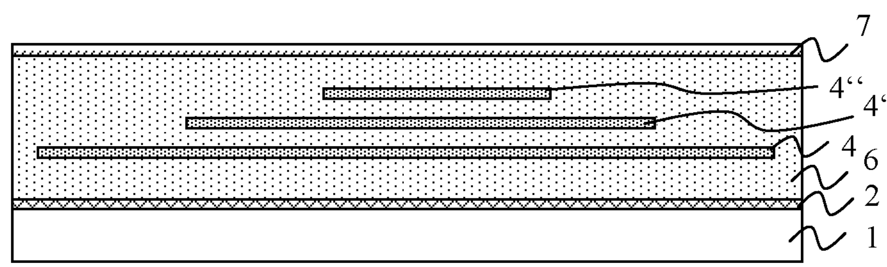
Figure 4S:
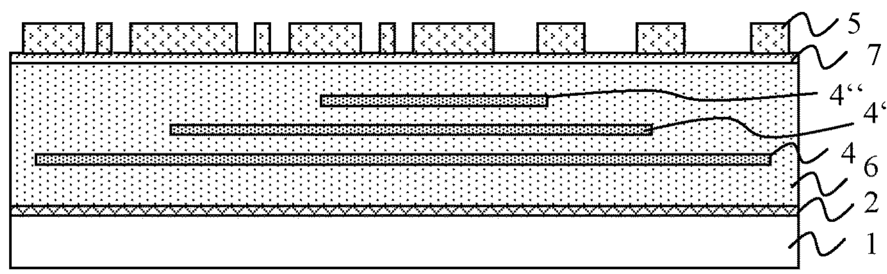
Figure 4T:
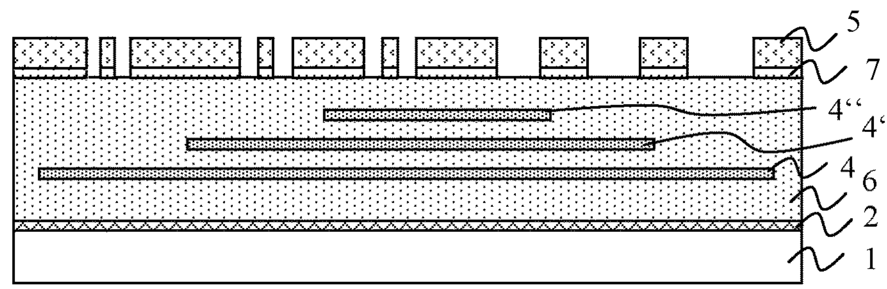
Figure 4U:
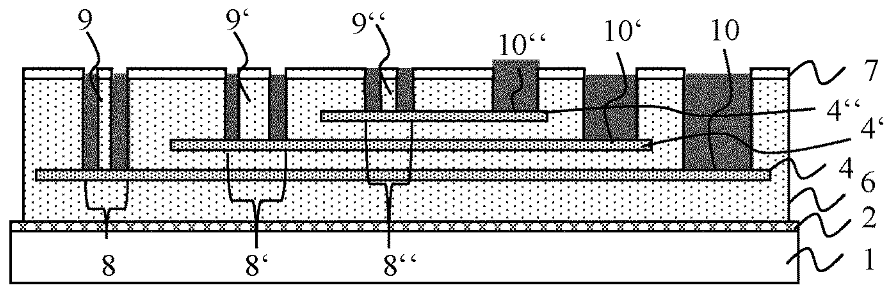
Figure 4V:
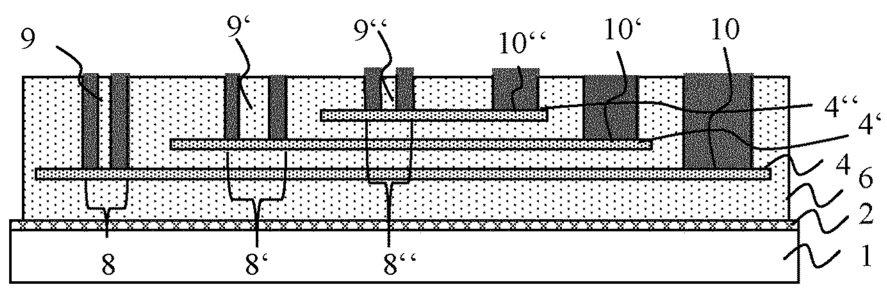
Figure 4W:
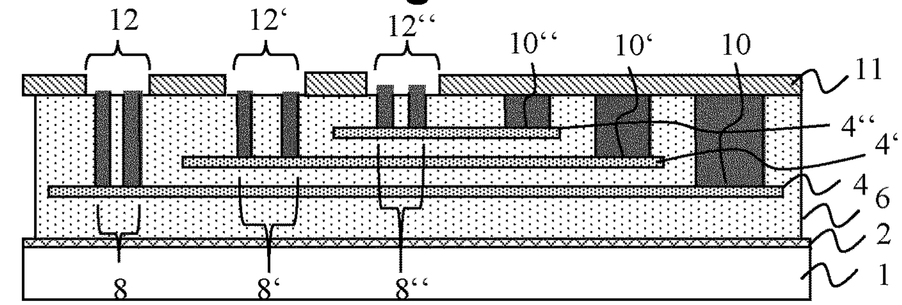
Figure 4X:
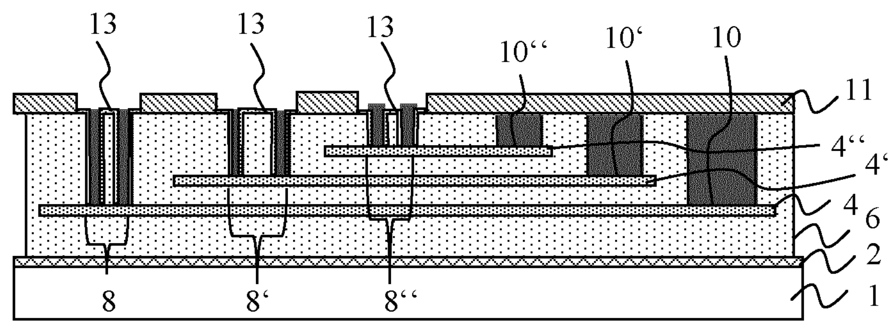
Figure 4Y:
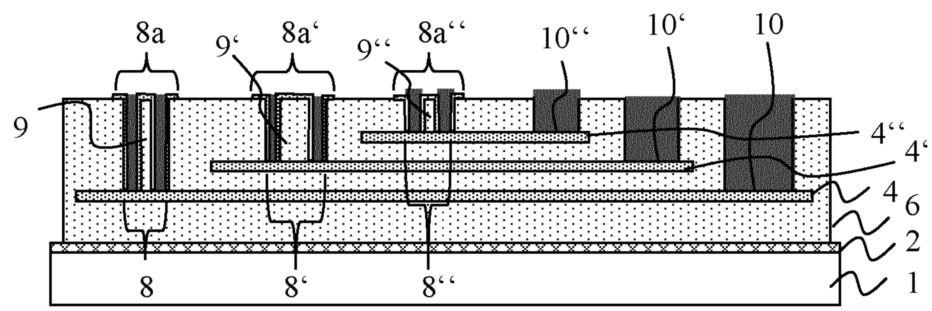
Figure 4Z:
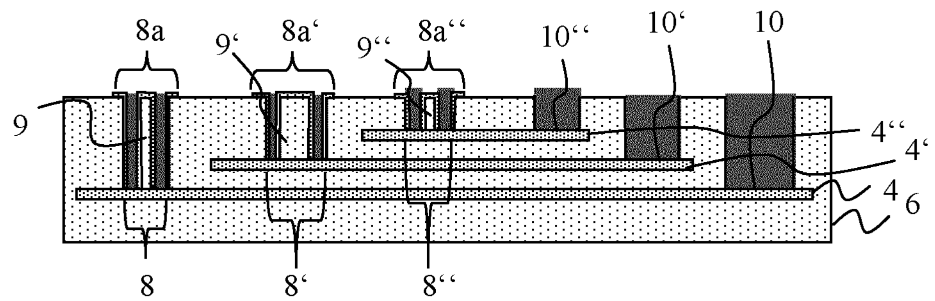

FIG. 4*a* to FIG. 4*z* show a first exemplary embodiment of a manufacturing process for manufacturing an electrode array according to the invention. It should be noted that the embodiment of FIG. 4 uses preferred method process parameters as an example only. Neither the used materials nor the applied processes nor the applied process parameters described in this description of the subsequent Figures limit the scope of the invention.

According to FIG. 4*a*, a substrate comprises a Si wafer 1 and an additional sacrificial layer 2 that comprises TiW and Al. This TiW/Al layer 2 is preferably obtained by a sputtering process, for instance a magnetron sputtering process. The TiW layer 2 has a thickness of 200 nanometer (nm) and the Al layer has a thickness of 1 microns (μm).

In FIG. 4*b*, a bottom insulating layer 3 is applied directly on top of the TiW/Al layer 2. The bottom insulating layer 3 preferably has a thickness d1 of 10 μm. The bottom insulating layer 3 is a PI layer, preferably PI2611 material that may be applied by a PI spin-coating process. A substrate dehydration of 5 minutes (min) at 100 degree Celsius (° C.) may be applied. The spin-coating of the PI may be applied with 1400 rounds-per-minute (rpm). Additionally, a soft bake process with a first duration of 5 min at 65° C. and a second duration of 5 min at 95° C. may be applied. The soft bake process is followed by a hard bake process with a third duration of 1 hour (h) at 300° C. under N2 atmosphere. Alternatively, an inkjet-printing process may be applied to obtain the bottom insulating layer 3.

In FIG. 4*c*, a layer 4 of electrically conducting material is applied directly on top of the bottom insulating layer 3. The layer 4 of electrically conducting material comprises a Ti layer of 20 nm thickness, a Pt layer of 100 nm thickness and further Ti layer of 10 nm thickness. This layer 4 of electrically conducting material may be obtained in a sputtering process, preferably a magnetron sputtering. Argon (Ar) etching can be applied for 10 seconds (s) prior the deposition of the conductive layer, because Ar as noble gas may not react with the substrate material, but it may prepare the polymeric surface through cleaning and roughening for a better metallic adhesion.

In FIG. 4*d*, a photoresist layer 5 is directly applied on top of the layer 4 of electrically conducting material. The photoresist layer 5 may have a thickness of 2 μm and may comprise photoresist material AZ9221. A direct writing exposure dose is 120 Milli-Joule (mJ) per square-centimeter ($cm^2$). A development and reflow process of the photoresist layer 5 is applied for 2 min at 115° C.

This photolithography process according to FIG. 4*d* may be followed by an ion beam etching process as indicated in FIG. 4*e*. The ion beam etching process can be used to pattern the layer 4, preferably to reduce its length and for forming conductive traces 16, 16', 16" (not shown) and further pads on a first layer 4 if required based on a planned wiring layout.

In FIG. 4*e*, an Ar ion etching is used at 2.5 min at a tilting degree of 30°. The applied power is 800 Milli-Ampere (mA) per $cm^2$ and 500 Volts (V). In FIG. 4*f*, the photoresist layer 5 has been removed using oxygen plasma at 500 Watts (W) for 30 s. The photoresist remover, preferably Remover 1165, is then applied for 25 minutes at 70° C.

In FIG. 4*g*, a layer 6 of insulating material is applied directly on top of the layer 4. The layer 6 may have a thickness d2 of 5 μm. The layer 6 is a PI layer, preferably PI2611, that is applied by another PI spin-coating process at 2200 rpm. Additionally, a soft bake process with a first duration of 5 min at 65° C. and a second duration of 5 min at 95° C. is applied. The soft bake process is followed by a hard bake process with a third duration of 1 hour at 300° C. The insulating layer 6 and the bottom insulating layer 3 encapsulate the layer 4. Following the layers 6 and 3 are indicated by one insulating layer 6.

In FIG. 4*h*, a layer 4' of electrically conducting material is applied directly on top of the insulating layer 6. The layer 4' comprises a Ti layer of 20 nm thickness, a Pt layer of 100 nm thickness and a further Ti layer of 10 nm thickness. This electrically conducting layer 4' is obtained in a sputtering process, preferably a magnetron sputtering. Therefore, again an argon (Ar) etching may be applied for 10 s before the metal deposition.

In FIG. 4*i*, another photoresist layer 5 is directly applied on top of the layer 4'. The photoresist layer 5 has a thickness of 2 μm and preferably comprises the photoresist material AZ9221. A direct writing exposure dose is at 120 mJ per $cm^2$. A development and reflow process of the photoresist layer 5 may be applied for 2 min at 115° C.

This photolithography process according to FIG. 4*i* is followed by an ion beam etching process as indicated in FIG. 4*j*. The ion beam etching process is used to pattern the layer 4', preferably to reduce its length and for forming conductive traces 16, 16', 16" (not shown) and pads at a second conductive layer 4' of the electrode array. In FIG. 4*j*, an Ar ion etching is used at 2.5 min at a tilting degree of 30 degree (°). The applied power is 800 mA per $cm^2$ and 500 V. In FIG. 4*k*, the photoresist layer 5 has been removed using oxygen plasma at 500 W for 30 s. The photoresist remover, preferably Remover 1165, is then applied for 25 minutes at 70° C.

In FIG. 4*l*, another layer 6 of insulating material is applied directly on top of the layer 4'. This layer 6 has also a thickness d2 of 5 μm. The layer 6 is also a PI layer, preferably PI2611 that is applied by another PI spin-coating process with 2200 rpm. Additionally, a soft bake process with a first duration of 5 min at 65° C. and a second duration of 5 min at 95° C. is applied. The soft bake process is followed by a hard bake process with a third duration of 1 hour at 300° C. The insulating layer 6 and the applied other layer 6 encapsulate the layer 4'. Following the layer 6 indicates all applied insulating layers.

In FIG. 4*m*, a layer 4" of electrically conducting material is applied directly on top of the insulating layer 6. The layer 4" also comprises a Ti layer of 20 nm thickness, a Pt layer of 100 nm thickness and a further Ti layer of 10 nm thickness. This electrically conducting layer 4" is obtained in a sputtering process, preferably a magnetron sputtering. Therefore, again argon (Ar) etching is applied for 10 s before the metal deposition.

In FIG. 4*n*, another photoresist layer 5 is directly applied on top of the layer 4". The photoresist layer 5 has a thickness of 2 μm and preferably comprises the photoresist material AZ9221. A direct writing exposure dose is at 120 mJ per $cm^2$. A development and reflow process of the photoresist layer 5 is applied for 2 min at 115° C.

This photolithography process according to FIG. 4*n* is followed by an ion beam etching process as indicated in FIG. 4*o*. The ion beam etching process is used to pattern the layer 4", preferably to reduce its length and for forming conductive traces 16, 16', 16" (not shown) and pads at a third conductive layer 4" of the electrode array. In FIG. 4*o*, an Ar ion etching is used at 2.5 min at a tilting degree of 30°. The applied power is 800 mA per $cm^2$ and 500 Volts. In FIG. 4*p*, the photoresist layer 5 has been removed using oxygen plasma at 500 W for 30 s. The photoresist remover, preferably Remover 1165, is then applied for 25 minutes at 70° C.

In FIG. 4*q*, another layer 6 of insulating material is applied directly on top of the layer 4". This layer 6 has a thickness d1 of 10 μm. The layer 6 is also a PI layer, preferably PI2611 that is applied by another PI spin-coating process with 1400 rpm. Additionally, a soft bake process with a first duration of 5 min at 65° C. and a second duration of 5 min at 95° C. is applied. The soft bake process is followed by a hard bake process with a third duration of 1 hour at 300° C. The insulating layer 6 and the applied other layer 6 encapsulate the layer 4". Following the layer 6 indicates all applied insulating layers.

According to FIG. 4*r*, a Si hard mask layer 7 is directly applied on top of the insulating layer 6. This Si layer 7 is applied by sputtering, preferably a magnetron sputtering process. The Si layer 7 has a thickness of 1 μm.

According to FIG. 4*s*, another photo resist layer 5 is directly applied on top of the Si layer 7. The photoresist layer material is preferably AZ9221 having a layer thickness of 2 μm. An alignment with the underlying layer(s) is obtained herein. According to FIG. 4*t*, a Si dry etch process is applied to pattern the Si layer 7.

In FIG. 4*u*, a PI and photoresist dry etch process is applied that patterns the whole insulating layer 6 at once. This etching process is applied to the entire thickness of the insulating layer 6 to obtain the full electrode array shaping. Preferably an inductively coupled plasma (ICP) etching process is used. By patterning the insulating layer 6, the insulating layer 6 is removed to expose contact areas 8, 8', 8" each at an electrically contacting layers 4, 4', 4". In FIG. 4*u*, the applied Si hard mask 7 is defined in a manner that insulating material remains in regions 9, 9', 9" at each contact area 8, 8', 8". As a result, pillars 9, 9', 9" remains in the contact area 8, 8', 8". This method step is advantageous, since Pt is inert to the oxygen plasma etching process and thus Pt acts as an etch-stop layer. Au as a conductive material layer 4 would also act as an etch-stop layer. Au is not as good as Pt as an etch-stop layer, so Pt is preferred herein. Otherwise other techniques may be applied to not damage the Au layer, e.g. an additional protection layer of Si on top of the Au layer.

In FIG. 4*u* also connecting areas 10, 10', 10" are shown. The layers 4, 4', 4" electrically connect each connecting area 10, 10', 10" to a contact area 8, 8', 8". These connecting areas 10, 10', 10" are used to interface an external processing unit (not shown) for obtaining or providing an electrical signal that is transmitted via the electrically conducting layer 4, 4', 4" to/from the contact areas 8, 8', 8".

In FIG. 4*v*, another Si dry etching process is applied to remove the remaining Si layer 7. In FIG. 4*w*, a stencil mask 11 is applied on top of the patterned insulating layer 6. The stencil mask 11 comprises openings 12, 12', 12". These openings 12, 12', 12" are aligned to the contact areas 8, 8', 8". As shown, openings 12, 12', 12" are not applied in the connecting areas 10, 10', 10" of the electrode array. However, the openings 12, 12', 12" may be applied in the connecting areas 10, 10', 10" of the electrode array to allow a better contact.

In FIG. 4*x*, a top layer 13 of electrically conducting material is applied to the electrode. Since only the openings 12, 12', 12" of the stencil mask 11 allow the appliance of the top layer 13 to the layered structure, the top layer 13 is applied in the contact area 8, 8', 8", especially for covering the remaining regions 9, 9', 9" in the contact area 8, 8', 8". The top layer 13 is applied by a sputtering process, preferably a magnetron-sputtering through the stencil mask 11. The top layer 13 is applied with Ar etching of 10 s and a Pt layer of 150 nm covering the remaining pillar 9, 9', 9". Since remaining insulating material is located inside the contact area 8, 8', 8", the material amount used for providing the top layer 13 is drastically reduced and the manufacturing costs are reduced.

In FIG. 4*y*, the stencil mask 11 is removed. Since the top layer 13 is in direct contact with the contact areas 8, 8', 8", the contact areas 8, 8', 8" are lifted to the level of the main surface 14 of the electrode array and so, lifted contact areas 8*a*, 8*a'*, 8*a"* are obtained. The electrode array of FIG. 4 has contact areas 8*a*, 8*a'*, 8*a"* that reduce the tissue-electrode distance and thus reduce signal transmission losses.

In FIG. 4*z*, an anodic dissolution process is applied to remove the substrate 1 and the TiW/Al layer 2. Therefore, a sodium chloride (NaCl) solution and a Pt counter electrode are used with a voltage for 0.8 Volts for 4 hours to 8 hours. The electrode array is finally fished from the NaCl bath, rinsed with DI-$H_2O$, and dried with a $N_2$-gun.

The inventive implantable electrode has lifted contact areas 8*a*, 8*a'*, 8*a"*, also referred to as stimulating elements or electrodes that are each aligned in a planar manner in vertical alignment. This allows a reduced constant distance between the nervous tissue and all respective contact area 8*a*, 8*a'*, 8*a"* that reduces failures when recording or stimulating the tissue with an electric signal. By using this multi-layered structure, a higher density and a higher spatial resolution is obtained.

It should be noted that FIG. 4 proposes one contact area 8, 8*a* for each layer 4 of electrically conducting material. The invention is not restricted thereto. A plurality of contact areas 8, 8*a* is preferred to increase the density of the electrode array.

Figure 5A:
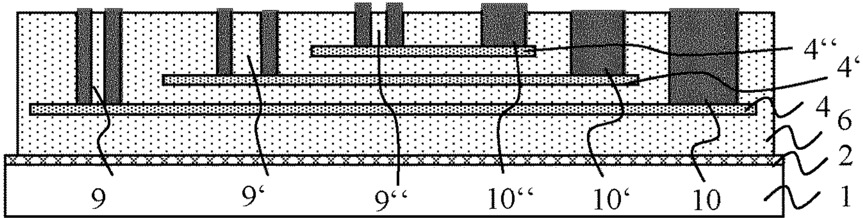
FIG. 5*a*-5*f* show a second exemplary embodiment of a manufacturing process for manufacturing a multi-layered electrode array according to the invention.

FIG. 5*a* to FIG. 5*f* show a second exemplary embodiment of a manufacturing process for manufacturing an electrode array according to the invention. This second embodiment comprises is not shown completely. In particular, the identical method steps as described with respect to the first embodiments for manufacturing an electrode array according to FIG. 4*a* to FIG. 4*u* are not shown with respect to the second embodiment to avoid an unnecessary repetition. FIG. 5*a* corresponds to FIG. 4*v* and is described in details above.

Figure 5B:
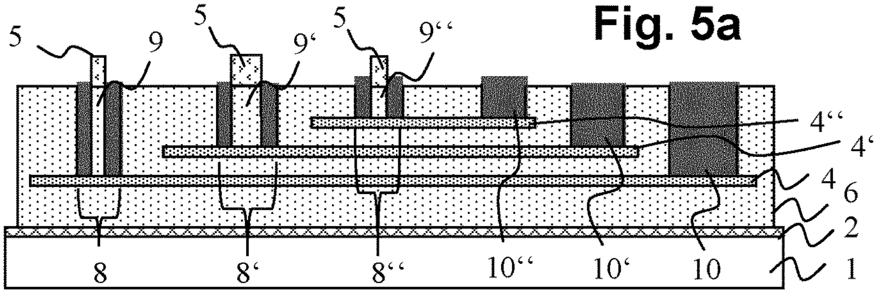

In contrast to the further method steps according to the first embodiment for manufacturing an electrode array, in the second embodiment for manufacturing an electrode array another photolithography step is processed in FIG. 5*b*. Therefore, a photoresist layer 5 is applied on top of each region 9, 9', 9" (pillars) of remaining insulating material 6. The photo-resist layer 5 has a thickness of 8 μm. The photoresist layer 5 is preferably AZ9260 that is applied with 2800 rpm. A direct writing exposure dose of 320 mJ per $cm^2$ is preferably applied.

Figure 5C:
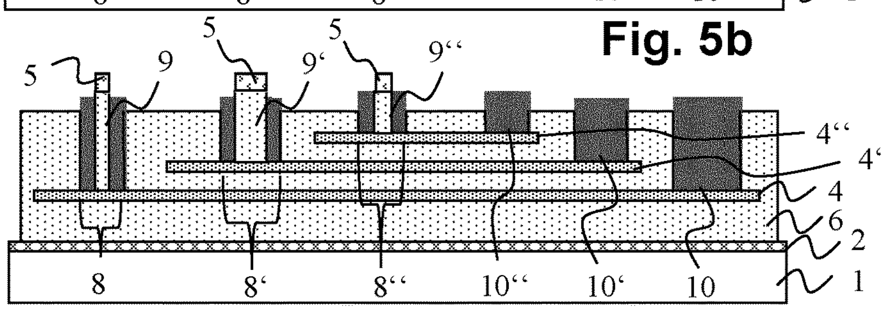
Figure 5D:
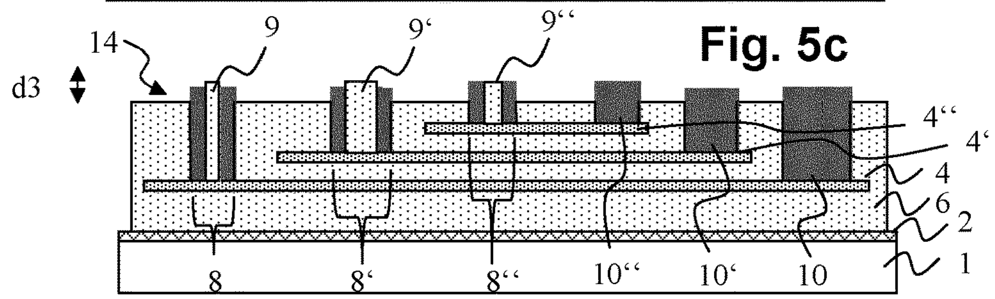

In FIG. 5*c*, a PI dry etching process is applied for reducing the thickness of the insulating material 6. Preferably, the thickness is reduced by 5 to 6 μm. By using the photoresist 5 as applied on top of the regions 9, 9, 9", the thickness of the insulating material 6 below the region 9, 9', 9" (pillars) is not reduced. This results in a protrusion of the pillars 9, 9', 9" above a main surface 14 with a protrusion distance d3 as shown in FIG. 5*c*. With this etching process, the protrusion distance d3 can be adjusted by the manufacturing steps according to FIG. 5*b* to FIG. 5*c* and is thus applicable to the individual application in which the electrode array should be used. A main surface of the electrode array is an outer surface of the electrode array that faces towards a nervous tissue (not shown). In FIG. 5*d* the photoresist layer 5 is removed, preferably by using a photoresist remover, e.g. Remover 1165 that is applied for 15 min at 70° C.

Figure 5E:
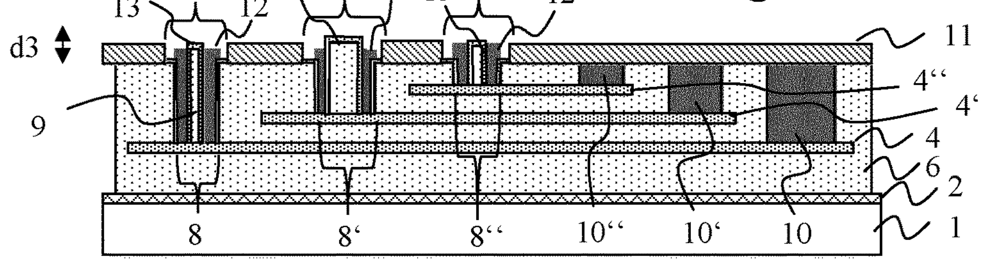
Figure 5F:
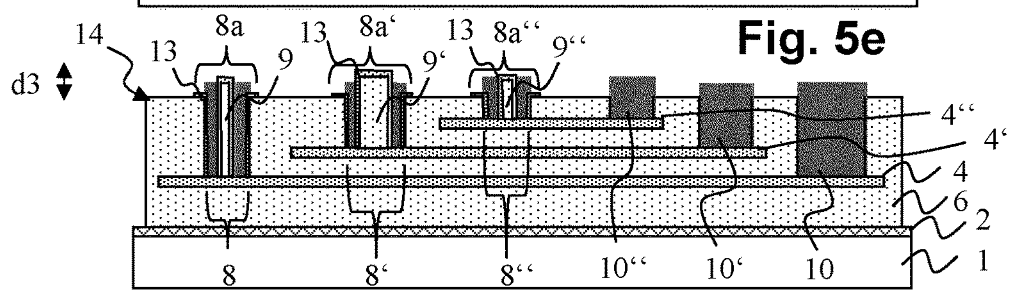

The manufacturing steps as shown in FIG. 5*e* and FIG. 5*f* correspond to the manufacturing step as shown in FIG. 4*x* to FIG. 4*y*. To avoid unnecessary repetitions, these steps according to FIG. 5*e* and FIG. 5*f* will not be described hereinafter. Finally (not shown in FIG. 5), the substrate layer 1 and the Ti/Al layer 2 are removed as already described in FIG. 4*z* to obtain the inventive electrode array.

The second embodiment according to FIG. 5*a* to FIG. 5*f* differs from the first embodiment according to FIG. 4*a* to FIG. 4*z* in that the lifted contact areas 8*a*, 8*a'*, 8*a"* are protruded from the main surface 14 with a protrusion distance d3. This protrusion distance d3 increases the stability of the position of the electrode array when placed in a nervous tissue. Also, it reduces signal degradation when providing/obtaining an electric signal to/from the nervous tissue (not shown) and thus the stimulation/recording is provided in a higher efficiency.

Figure 6:
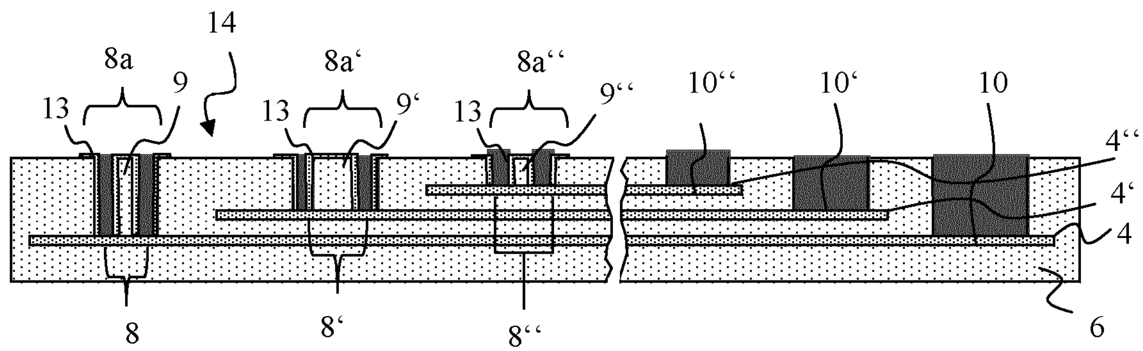
FIG. 6 shows a first exemplary embodiment of an implantable electrode array according to the invention in side view.

FIG. 6 shows a first exemplary embodiment of an implantable electrode array according to the invention in side view. FIG. 6 may refer to an implantable electrode array as manufactured according to the manufacturing process shown in FIG. 4. The first embodiment comprises three layers 4, 4', 4" of an electrically conducting material, preferably Pt, Ti, Pt/IR-alloy or Au. Each of the layers 4, 4', 4" comprise one contact area 8, 8', 8". The contact area 8, 8', 8" that have been lifted to obtain lifted contact areas 8*a*, 8*a'*, 8*a"* as described with reference to FIG. 4. The lifted contact areas 8*a*, 8*a'*, 8*a"* are on the same level as the main surface 14. So the distance between the main surface 14 of the electrode array with a nervous tissue (not shown) is equal with respect to each of the lifted contact areas 8*a*, 8*a'*, 8*a"*. So, a main factor of degrading the signal transmission—the tissue-electrode-distance—is eliminated with this first embodiment according to FIG. 6. So, the aspect ratio between the diameter of the contact areas 8*a*, 8*a'*, 8*a"* and the encapsulating thickness of the layer 6 of the insulating material is eliminated and the efficiency of a stimulating/recording of the nervous tissue is independent on the distance between the contact area 8*a*, 8*a'*, 8*a"* and the nervous tissue. This distance is now independent of an encapsulation-openings aspect ratio.

In FIG. 6 also the connecting areas 10, 10', 10" are show. Each of the layers 4, 4', 4" comprises at least one connecting area 10, 10', 10". The connecting areas 10, 10', 10" are used to provide an electrical signal transmitted via the layers 4, 4', 4" from/to a processing unit (not shown). The processing unit is used to process/generate the electrical signal as will not be described in greater details herein. The number of contact areas 8*a*, 8*a'*, 8*a"* correspond to the number of connecting areas 10, 10', 10", so that an electrical signal provided/obtained from/to a dedicated contact area 8*a*, 8*a'*, 8*a"* is obtained/provided to/from a dedicated connecting area 10, 10', 10". It is indicated in FIG. 6 that the longitudinal alignment between the contact areas 8*a*, 8*a'*, 8*a"* and the connecting areas 10, 10', 10" can have a greater dimension than shown. So the longitudinal alignment of the MEA can be extended for an easier implanting and to avoid unnecessary large cuts in a nervous tissue.

Figure 7:
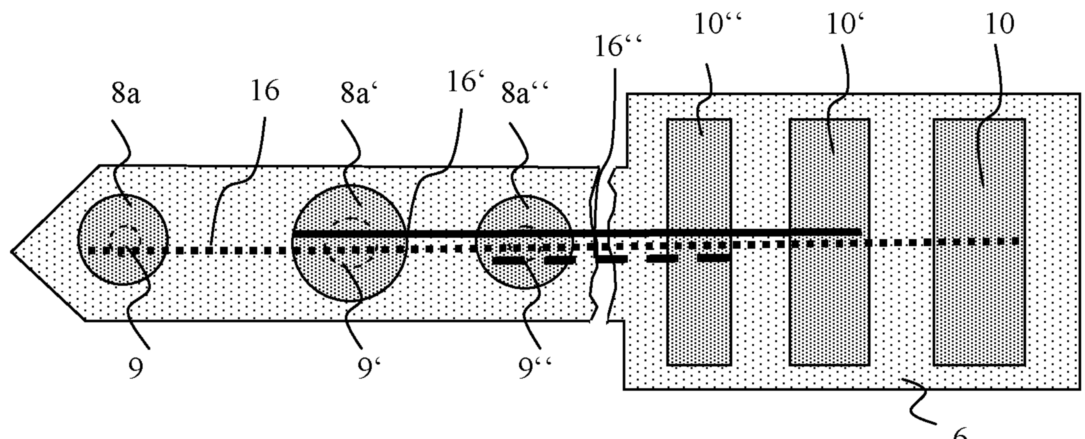
FIG. 7 shows the first exemplary embodiment of an implantable electrode array according to FIG. 6 in top view.

FIG. 7 shows the first exemplary embodiment of an implantable electrode array according to FIG. 6 in top view. As can be seen in FIG. 7, the pillars 9, 9', 9" of remaining insulating material 6 are shown with dotted lines to indicate the lifting of the contact areas 8, 8', 8" by covering the pillars 9, 9', 9" with a top layer 13 to obtain the lifted contact areas 8*a*, 8*a'*, 8*a"*. The diameter of the lifted contact areas 8, 8', 8" are thus adjustable very easily.

In FIG. 7, the implantable electrode array has a lateral alignment that is much smaller than its longitudinal alignment. Furthermore, a part of the electrode array in which the contact areas 8*a*, 8*a'*, 8*a"* are located has a smaller lateral alignment than a part of the electrode array in which the connecting areas 10, 10', 10" are located to enable an easy implanting if required. In fact, the lateral alignment of the electrode array in which the contact areas 8*a*, 8*a'*, 8*a"* are located may be limited to the outer dimensions of the contact areas 8*a*, 8*a'*, 8*a"* and a small edge of insulating material 6 to reduce the required space when implanting this electrode array in a nervous tissue (not shown). FIG. 7 also shows the potential of this inventive method. Here the trace 16 can easily pass under each contact area 8*a'*, 8*a"* (electrode) and trace 16', 16" and pad 10', 10" above to connect the contact area 8*a* to the respective pad 10. Thus, the bottom trace 16 can connect the most distant contact area 8*a* with the most distant pad 10.

Figure 8:
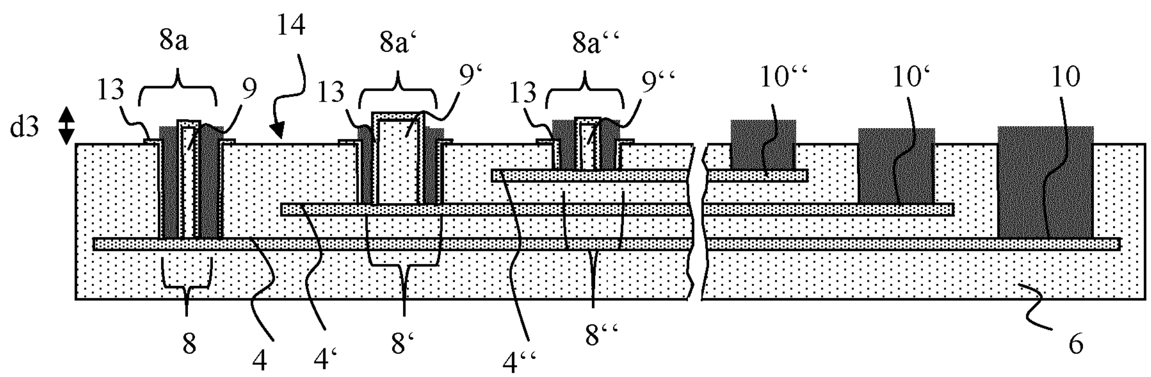
FIG. 8 shows a second exemplary embodiment of an implantable electrode array according to the invention in side view.

FIG. 8 shows a second exemplary embodiment of an implantable electrode array according to the invention in side view. FIG. 8 may refer to an implantable electrode array as manufactured according to the manufacturing process shown in FIG. 5. In FIG. 8, a cross-section view of the electrode array is shown. A difference between FIG. 6 and FIG. 8 is given by a protrusion distance d3 of the lifted contact areas 8*a*, 8*a'*, 8*a"* in view of the main surface 14 of the electrode array. The protrusion distance d3 can be adjustable via the photolithography processes as shown and described with FIG. 5*b* to FIG. 5*c*.

Figure 11:
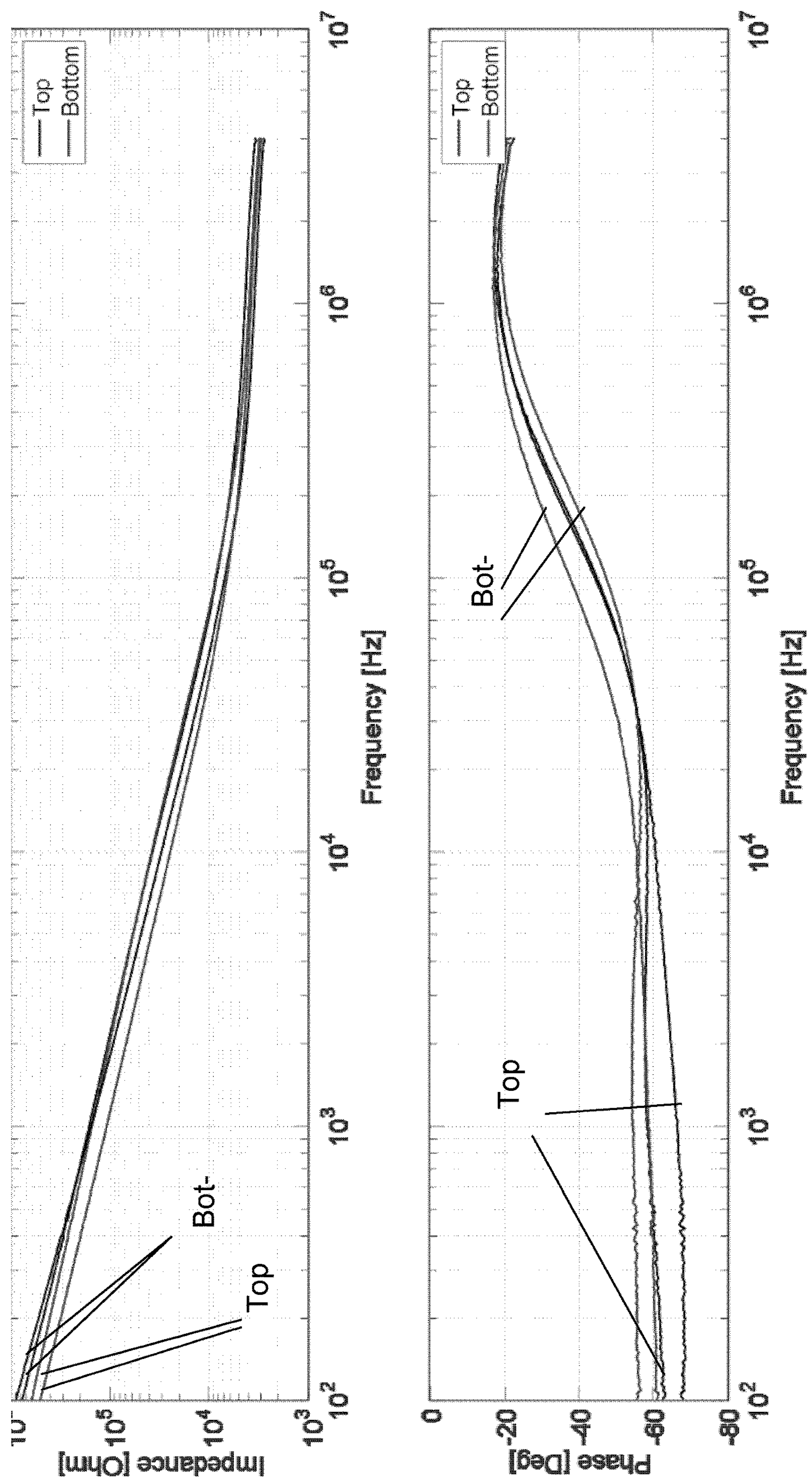
FIG. 11 shows an exemplary impedance spectrometry response characteristics of a multi-layered 3D electrode array according to the invention.
Figure 12:
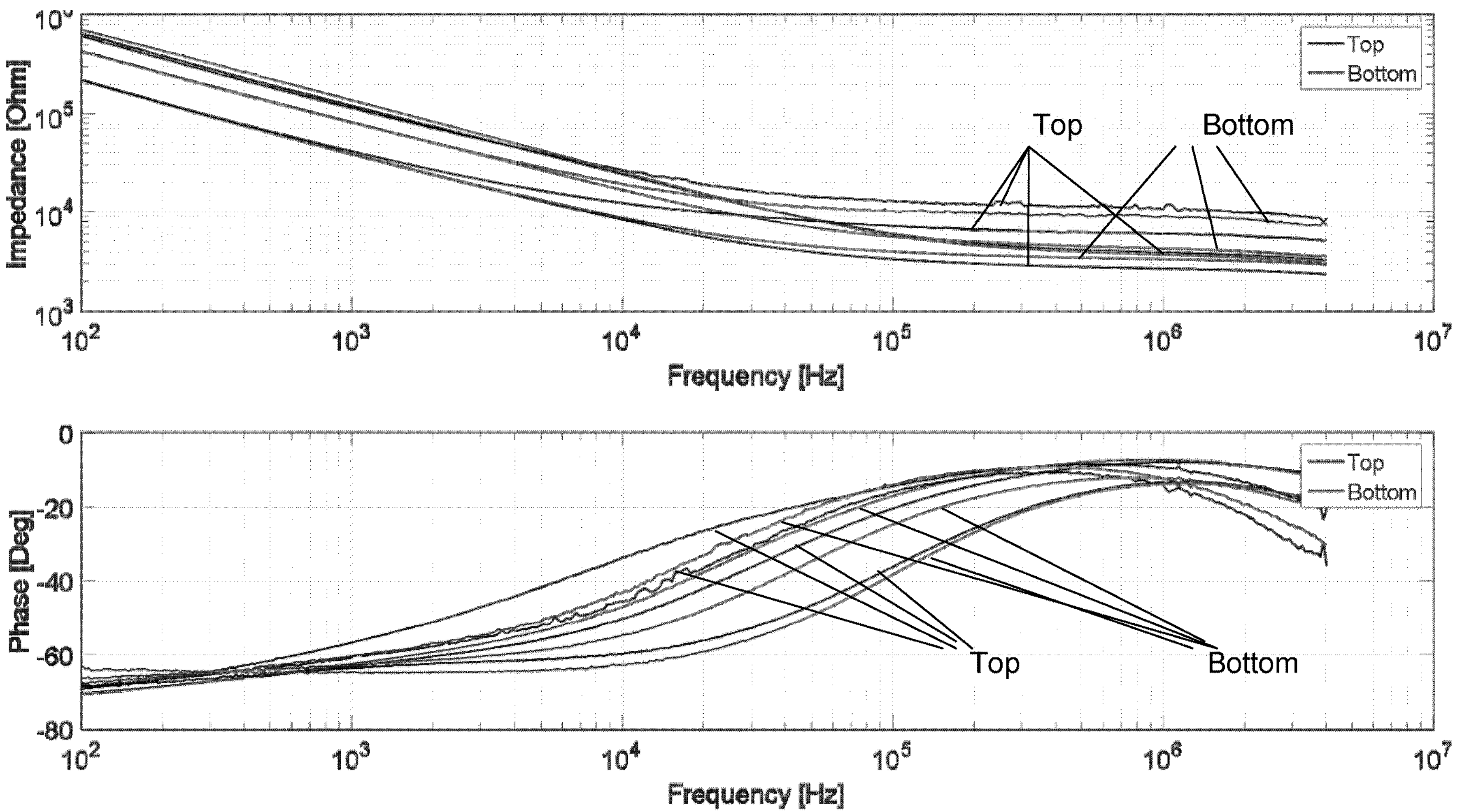
FIG. 12 shows an exemplary impedance spectrometry characteristics of a multi-layered planar electrode array according to the prior art.

The electrical characteristics of a two-layered 3D electrode as may also be manufactured according to FIG. 4 (or FIG. 5) are shown in FIG. 11. The electrical characteristics of a conventional two-layered planar electrode are shown in FIG. 12 to compare the improvement over the conventional electrode.

FIG. 9*a* to FIG. 9*j* show an exemplary embodiment for fabricating a stencil mask 11 used for manufacturing an electrode array according to the invention, e.g. for producing the electrode according to the manufacturing process steps as shown in FIG. 4*w*, FIG. 4*x* and FIG. 5*e*.

Figure 9A:
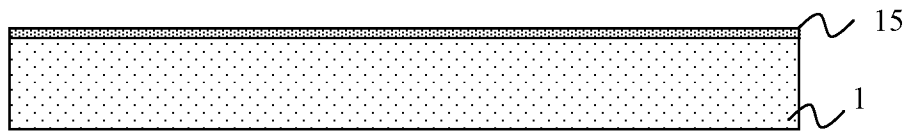
FIG. 9*a*-9*j* show an exemplary embodiment for fabricating a stencil mask used for manufacturing an electrode array according to the invention.
Figure 9B:
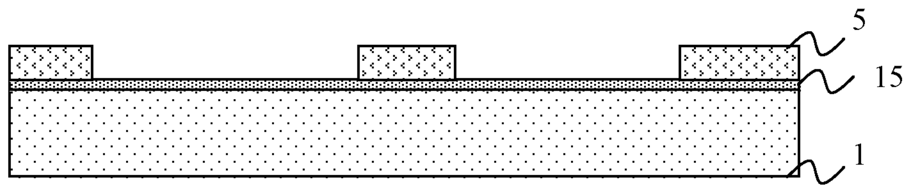

In FIG. 9*a*, a Si wafer 1 is provided having a Silicone dioxide ($SiO_2$) layer 15. This $SiO_2$ layer 15 may have a thickness of 1 μm and is preferably thermally grown by a Si wet oxidation process. In FIG. 9*b*, a photoresist layer 5 is directly applied on the $SiO_2$ layer 15 in a photolithography process. Preferably, AZ 9221 photoresist is applied with 4200 rpm. A direct writing exposure dose of 120 mJ per $cm^2$ is applied.

Figure 9C:
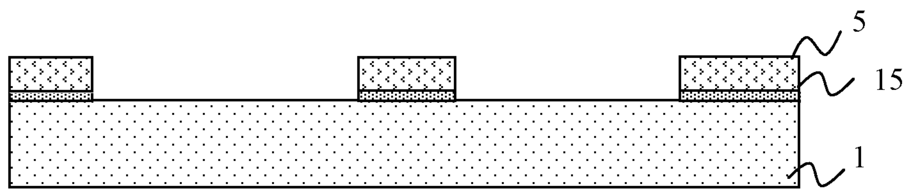
Figure 9D:
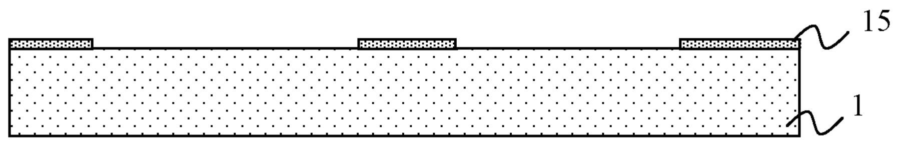
Figure 9E:
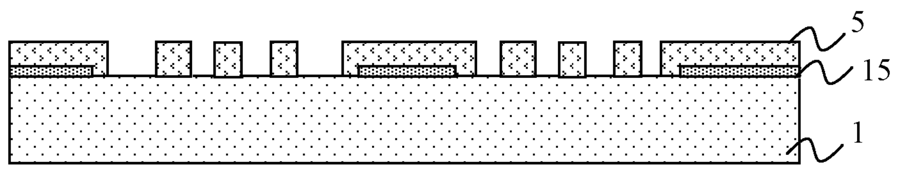

In FIG. 9*c*, a $SiO_2$ dry etching process, preferably using an inductively coupled plasma (ICP) etching process, is applied to pattern the $SiO_2$ layer 15. In FIG. 9*d*, the photo resist layer 5 is removed, preferably by oxygen plasma etching process that is applied 5 min at 600 W. In FIG. 9*e*, a further photolithography process is applied using a photoresist layer 5. Preferably, AZ 9221 photoresist of a thickness of 4 μm is applied with 1100 rpm. A direct writing exposure dose of 160 mJ per $cm^2$ is applied.

Figure 9F:
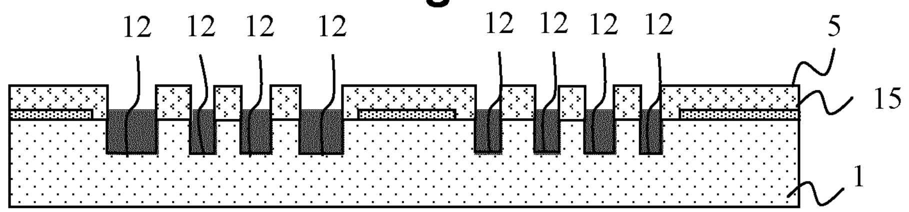
Figure 9G:
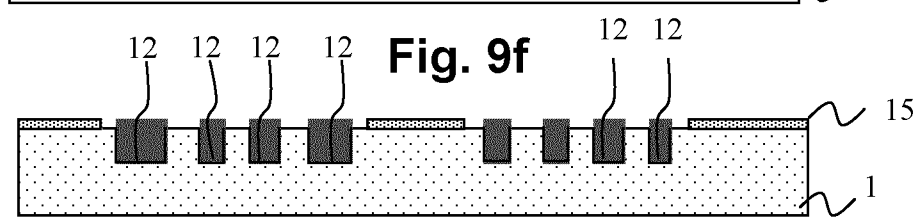

In FIG. 9*f*, a Si dry etching process is applied to obtain openings 12 in the stencil mask 11, preferably using an inductively coupled plasma (ICP) etching process. According to FIG. 9*g*, the photoresist layer 5 is removed, preferably by oxygen plasma etching that is applied 5 minutes at 600 Watts.

Figure 9H:
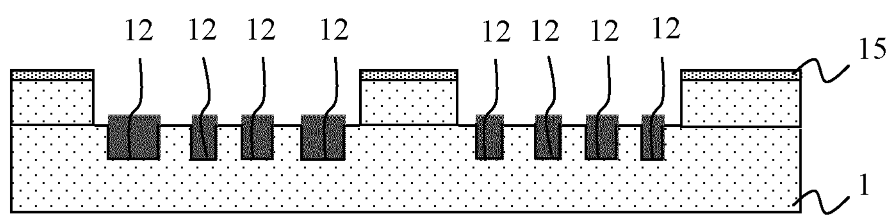
Figure 9I:
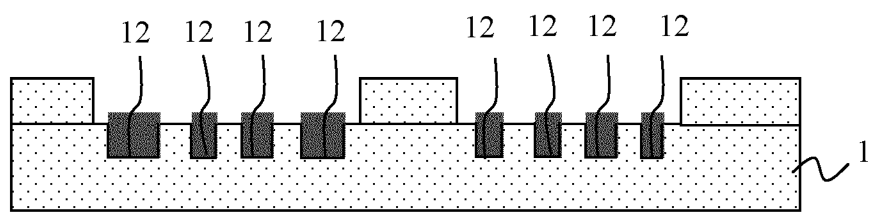
Figure 9J:
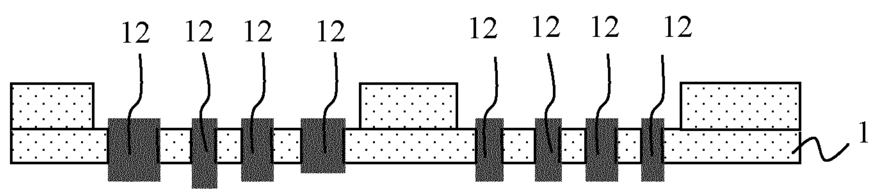

In FIG. 9*h*, a Si dry etching process, preferably ICP etching is applied. In FIG. 9*i*, a $SiO_2$ wet etching in buffered HF is applied to remove the $SiO_2$ layer 15. In FIG. 9*j*, a backside wafer grinding is applied for obtaining the final stencil mask 11 with the openings 12.

Figure 10:
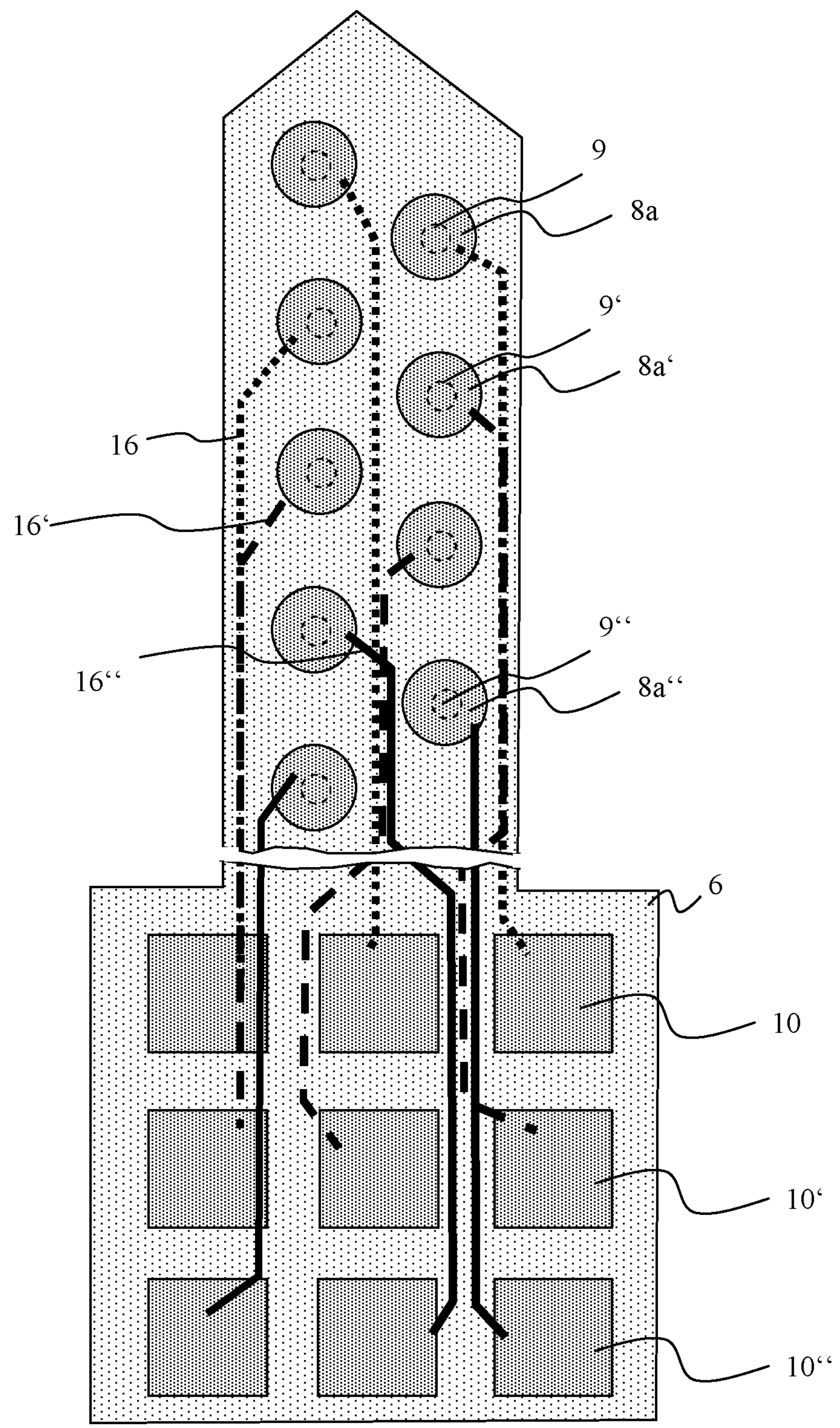
FIG. 10 shows a third exemplary embodiment of an implantable electrode array in top view according to the invention.

FIG. 10 shows a third exemplary embodiment of an implantable electrode array in top view according to the invention. In FIG. 10, the electrode array comprises nine contact areas 8*a*, 8*a*', 8*a*" that are electrically connected to connecting areas 10, 10', 10" in three different electrically conducting layers 4, 4', 4" (not shown). In FIG. 10, three contact areas 8*a* are arranged in an electrically conducting layer 4 (not shown) at a distal end of the implantable electrode array (top view perspective). For connecting these contact areas 8*a*, conductive traces 16 (dotted lines) are formed to connect each contact area 8*a* with a dedicated connecting area 10 that is located nearest to the contact area 8*a* (top view perspective) that results in a comparable total length of the conductive traces 16. Furthermore, three contact areas 8*a*' are arranged in an electrically conducting layer 4' (not shown) a middle portion of the part of the electrode array (top view perspective) in which the contact areas 8*a*, 8*a*', 8*a*" are located. For connecting these contact areas 8*a*', conductive traces 16' (dashed lines) are formed to connect each contact area 8*a*' with a dedicated connecting area 10'. Furthermore, three contact areas 8*a*" are arranged in an electrically conducting layer 4" (not shown) nearest to dedicated connecting area 10" (top view perspective). For connecting these contact areas 8*a*", conductive traces 16" (solid lines) are formed to connect each contact area 8*a*" with a dedicated connecting area 10". So, the overall (total) length of all the conductive traces 16, 16' 16" are equalized as much as possible. This equalization of the length ensures that parasitic effects-such as resistance values, capacitance values and inductance values-caused by the conductive material of each trace 16, 16', 16" is nearly the same. So, these parasitic effects of the traces 16, 16', 16" do not cause additional deviations in the characteristics of each signal transmission in dependence on a specific location of the contact area 8*a*, 8*a*', 8*a*" or the dedicated connecting area 10, 10', 10". So, the signals from different contact area 8*a*, 8*a*', 8*a*" or dedicated connecting area 10, 10', 10" are influenced by nearly the same parasitic effects in a comparable manner. As a result, the quality of the signal transmission is further increased and influences due to a specific location of the contact area 8*a*, 8*a*', 8*a*" are reduced.

The contact areas 8*a*, 8*a*', 8*a*" are lifted and protrude from the main surface 14 by at least 2 μm above the PI encapsulation layer 6.

In another embodiment (not shown) eight Pt contact areas 8*a*, 8*a*' are distributed over two different conductive layers 4, 4'. Four contact areas 8*a* are distributed over a first electrically conducting layers 4 and another four contact areas 8*a*' are distributed over a second electrically conducting layers 4'. All contact areas 8*a*, 8*a*' are lifted to the same level compared to a main surface 14 of the electrode array. This embodiment is used to compare the electrical characteristics of the inventive electrode array compared to conventional arrays.

FIG. 11 shows an exemplary impedance spectroscopy characteristic of a two-layered 3D electrode array according to the invention. As can be seen from the signal behaviors of FIG. 10, the impedance (and phase) behavior of the electrically conducting higher (top) layer 4' are nearly identical to the impedance (and phase) behavior of the electrically conducting lower (bottom) layer 4 over the frequency range of 100 Hz to 4 MHz. Thus, it can be concluded that the electric characteristic of the layers 4 and 4' are nearly identical and no variations exists in accordance to the position of the contact area 8*a*, 8*a*' on the MEA. Furthermore, due to the reduced distance between the nervous tissue and the main surface 14 of the electrode array, the recording signal-to-noise ratio could be increased and the stimulation voltage/current could be decreased. Thus, there is no difference in signal transmission behavior between the higher layer 4 and the lower layer 4' and the signal degradation is reduced for in-vivo applications.

FIG. 12 shows an exemplary impedance spectroscopy characteristics of a bi-layered electrode array according to the prior art for a direct comparison with the characteristics according to FIG. 11. This causes degrading of the signal transmission due to different distance values between the nervous tissue and the individual contact area. Here, the aspect ratio between the diameter of the contact areas 8 and the encapsulating thickness of the layer 6 of the insulating material highly influences the characteristics of the signal transmission and thus the efficiency of a stimulating/recording of the nervous tissue is dependent on the distance between the contact area 8 and the nervous tissue. The encapsulation-openings aspect ratio influences this distance in a disadvantageous manner.

FIG. 13 shows an exemplary impedance spectroscopy characteristic of a single-layered electrode array according to the invention. As can be seen from the signal behaviors of FIG. 13, the impedance values (and the phase values) of the individual contact area 8*a* of the electrically conducting layer 4 do not vary from another individual contact area 8*a* of this electrically conducting layer 4 over the monitored frequency range of 100 Hz to 4 MHz. So, the actual position of the contact area 8*a*, 8*a*' does not influence the signal transmission between a processing unit and a nervous tissue, due to the reduced distance between the nervous tissue and the main surface 14 of the electrode array.

FIG. 14 shows an exemplary impedance spectroscopy characteristic of a single-layered electrode array according the prior art for a direct comparison with the characteristic as shown in FIG. 13. This causes degrading of the signal transmission due to different distance values between the nervous tissue and the individual contact area. Here, the aspect ratio between the diameter of the contact areas 8 and the encapsulating thickness of the layer 6 of the insulating material highly influences the characteristics of the signal transmission and thus the efficiency of a stimulating/recording of the nervous tissue is dependent on the distance between the contact area 8 and the nervous tissue. The encapsulation-openings aspect ratio influences this distance in a disadvantageous manner.

The performed impedance spectroscopy on the inventive electrode array shows that a similar behaviour with respect to standard monolayer, flat Pt electrodes is obtained. So, the inventive MEA performance is comparable with known MEA structures, but can increase significantly the density of electrodes and the contact area behaviour with nervous tissue.

The proposed manufacturing can produce multi-layer MEA within one single dry etching step that also defines the outer shape of the electrode array without a need for cutting. With an extra step of photolithography and dry etching the electrodes can protrude from the encapsulation layer 6 to a desired protrusion distance d3.

Another advantage of the electrode array made in the coated insulating material 6 is a higher surface area due to the walls porosity of PI after the dry etching. This implies that the electrode array can have a better injection capacity with respect to flat electrodes. Furthermore, with this technique, no electroplating is needed, which means that there are fewer problems due to local mechanical mismatch of the conductive layers 4 and the insulating material layer 6. Electroplating is also more expensive as it involves more material to deposit to fill the entire volume of the openings, in order to reach the top surface of the MEA.

All features of all embodiments described, shown and/or claimed herein can be combined with each. Embodiments shown in a specific FIG. may be used as intermediate steps for embodiments shown in another FIG. Furthermore, single steps in an embodiment may be interchanged in that the sequence of the steps shown in the embodiment may be changed. Furthermore, single steps in an embodiment may be interchanged with steps of other embodiments.

While various embodiments of the present invention have been described above, it should be understood that they have been presented by way of example only, and not limitation. Numerous changes to the disclosed embodiments can be made in accordance with the disclosure herein without departing from the scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The invention claimed is:

1. A method for manufacturing an electrode comprising:

applying a layer of electrically conducting material above a substrate material for forming an electrically conductive trace;

forming an electrically conductive trace from the electrically conducting material;

applying a layer of insulating material directly on top of the layer of electrically conducting material for covering the electrically conductive trace;

patterning the layer of insulating material by partly exposing the layer of electrically conducting material for forming at least one contact area on the layer of electrically conducting material, wherein a mask for patterning the layer of insulating material defines a predefined region in a center of the at least one contact area at which the insulating material in the at least one contact area remains as a pillar in the center of the at least one contact area;

partly applying a top layer of electrically conducting material at the at least one contact area directly on top of the layer of insulating material for coating the remaining insulating material in the region to lift the contact area.

2. The method of claim 1, wherein the step patterning the layer of insulating material further includes:

covering the remaining insulating material in the at least one contact area using a photoresist material; and reducing the thickness of the uncovered regions of the layer of insulating material.

3. The method according to claim 1, wherein the step of partly applying of the top layer of electrically conducting material is obtained through respective openings in a stencil mask.

4. The method according to claim 1, wherein before processing the step of patterning the layer of insulating material:

a second layer of electrically conducting material is directly applied on top of the insulating material; and a second layer of insulating material is directly applied on top of second layer of electrically conducting material.

5. The method according to claim 4, wherein the step of applying of the second layer of electrically conducting material and the step of applying of the second layer of insulating material is at least once, or twice repeated, before the step of patterning the insulating material is processed.

6. The method according to claim 4, wherein the step of patterning of the layer of insulating material includes patterning of the second layer of insulating material at once by partly exposing the respective layer of electrically conducting material for obtaining at least one contact area on each layer of electrically conducting material, wherein the mask for patterning all the layers of insulating material defines a region in each contact area of each layer of the electrically conducting material at which the insulating material in the respective contact area remains.

7. The method according to claim 6, wherein the step of partly applying the top layer of electrically conducting material includes applying the top layer at each contact area for coating all the remaining insulating material in the region to lift each of the contact areas.

8. The method according to claim 1, wherein before processing the step of applying the layer of electrically conducting material a bottom layer of insulating material is applied directly on top of the substrate material.

9. The method according to claim 1, wherein the step of applying the layer of electrically conducting material further includes a patterning step.

10. The method according to claim 1, wherein the substrate material is removed to obtain the electrode.

* * * * *